US009770286B2

(12) United States Patent
Kase

(10) Patent No.: US 9,770,286 B2
(45) Date of Patent: Sep. 26, 2017

(54) ENERGY TREATMENT DEVICE

(71) Applicant: OLYMPUS CORPORATION, Shibuya-ku, Tokyo (JP)

(72) Inventor: Seigo Kase, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/074,518

(22) Filed: Mar. 18, 2016

(65) Prior Publication Data
US 2016/0199121 A1 Jul. 14, 2016

Related U.S. Application Data

(63) Continuation of application No. PCT/JP2015/050036, filed on Jan. 5, 2015.

(30) Foreign Application Priority Data

Jan. 16, 2014 (JP) ................. 2014-006108

(51) Int. Cl.
*A61B 18/14* (2006.01)
*A61B 17/32* (2006.01)
*A61B 18/12* (2006.01)

(52) U.S. Cl.
CPC .. *A61B 18/1442* (2013.01); *A61B 17/320092* (2013.01); *A61B 18/1206* (2013.01);
(Continued)

(58) Field of Classification Search
CPC .... A61B 2017/2905; A61B 2017/2918; A61B 2017/2932; A61B 18/1445; A61B 18/1442; A61B 2017/2937; B25B 7/02
See application file for complete search history.

(56) References Cited

U.S. PATENT DOCUMENTS 5,810,883 A * 9/1998 Lang .................. A61B 17/1608
600/564
6,139,561 A 10/2000 Shibata et al.
(Continued)

FOREIGN PATENT DOCUMENTS

DE 102006042985 A1 4/2007
JP 2000000249 A 1/2000
(Continued)

OTHER PUBLICATIONS

International Preliminary Report on Patentability (IPRP) including Written Opinion (in English) dated Jul. 28, 2016, issued in counterpart International Application No. PCT/JP2015/050036.
(Continued)

*Primary Examiner* — Jaymi Della
(74) *Attorney, Agent, or Firm* — Holtz, Holtz & Volek PC

(57) ABSTRACT

An energy treatment device includes a probe, a sheath unit, a fixed handle, a movable handle unit, a rotation axis, a jaw and a thickness-reduced portion. The thickness-reduced portion is one part of the jaw and is provided between the rotation axis and a distal end of the jaw. The thickness-reduced portion flexes in response to a reaction force when one part of the jaw receives the reaction force from a treatment target due to the opening and closing of the movable handle unit to the treatment target. The thickness-reduced portion prevents the deformation of the other parts of the jaw by flexing.

7 Claims, 14 Drawing Sheets

(52) U.S. Cl.
CPC ...... *A61B 18/1445* (2013.01); *A61B 18/1482* (2013.01); *A61B 18/1485* (2013.01); *A61B 2018/1452* (2013.01); *A61B 2018/1465* (2013.01)

(56) References Cited

U.S. PATENT DOCUMENTS

| | | | |
|---|---|---|---|
| 6,736,813 B2 * | 5/2004 | Yamauchi | A61B 18/1442 606/37 |
| 8,926,610 B2 | 1/2015 | Hafner et al. | |
| 2006/0259054 A1 | 11/2006 | Masuda et al. | |
| 2008/0215048 A1 * | 9/2008 | Hafner | A61B 17/2841 606/42 |
| 2013/0110155 A1 * | 5/2013 | Tsuchiya | A61B 17/28 606/205 |
| 2015/0164526 A1 * | 6/2015 | Bernhardt | B26B 13/12 606/205 |

FOREIGN PATENT DOCUMENTS

| | | |
|---|---|---|
| JP | 4727575 B2 | 7/2011 |
| WO | 2012128362 A1 | 9/2012 |
| WO | 2014001200 A1 | 1/2014 |

OTHER PUBLICATIONS

International Search Report (ISR) dated Apr. 7, 2015 issued in International Application No. PCT/JP2015/050036.
Japanese Office Action dated Oct. 20, 2015 issued in counterpart Japanese Application No. 2014-006108.

* cited by examiner

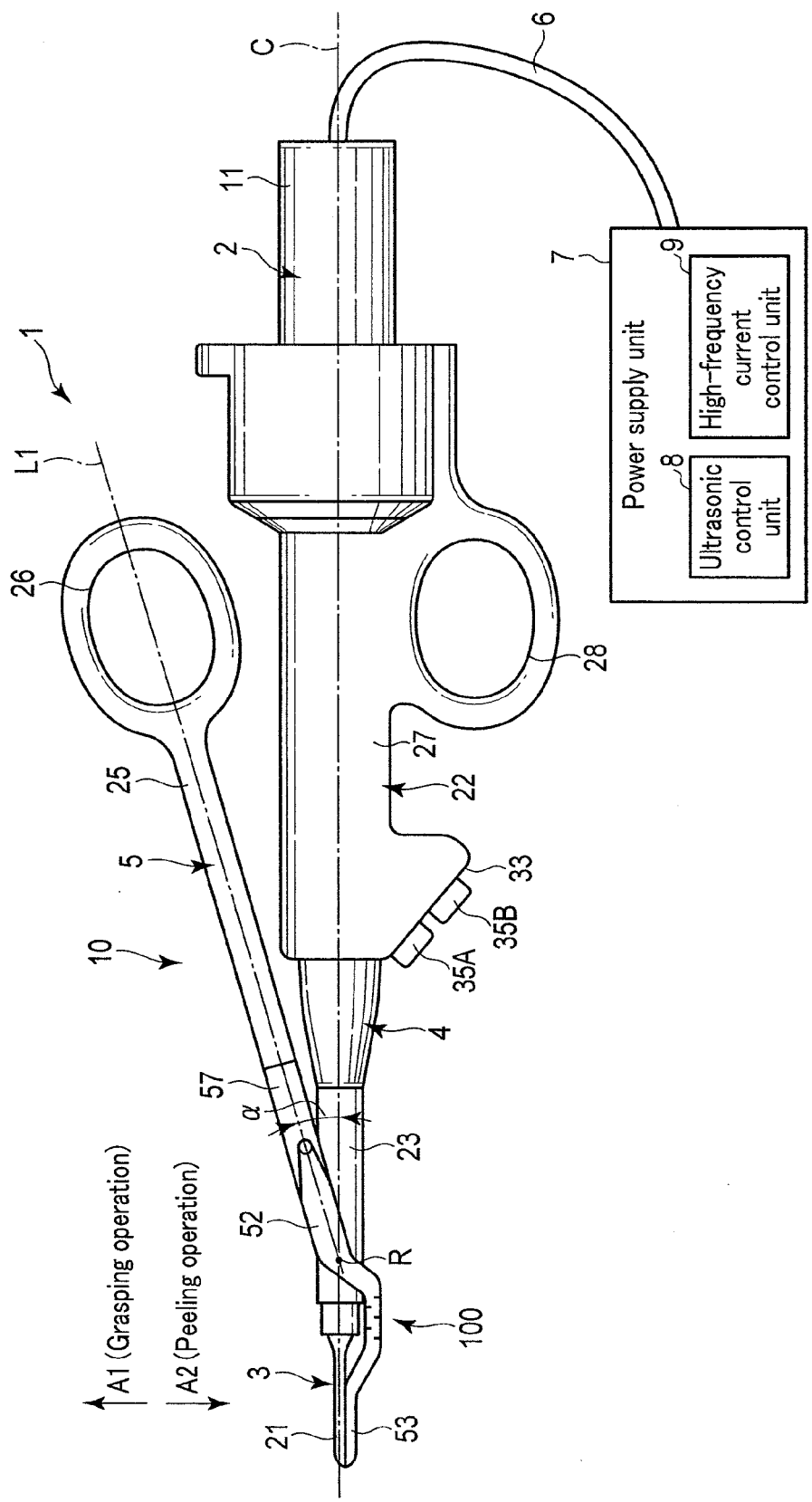
F I G. 1

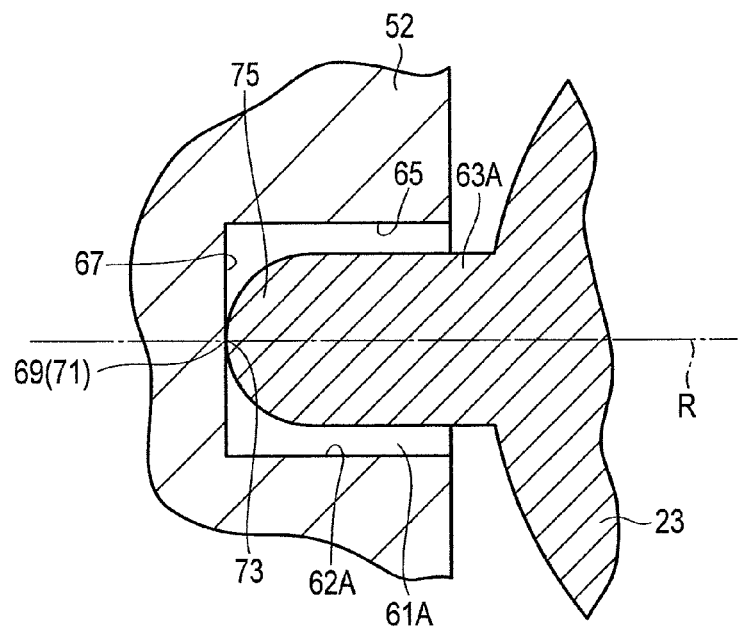
F I G. 8
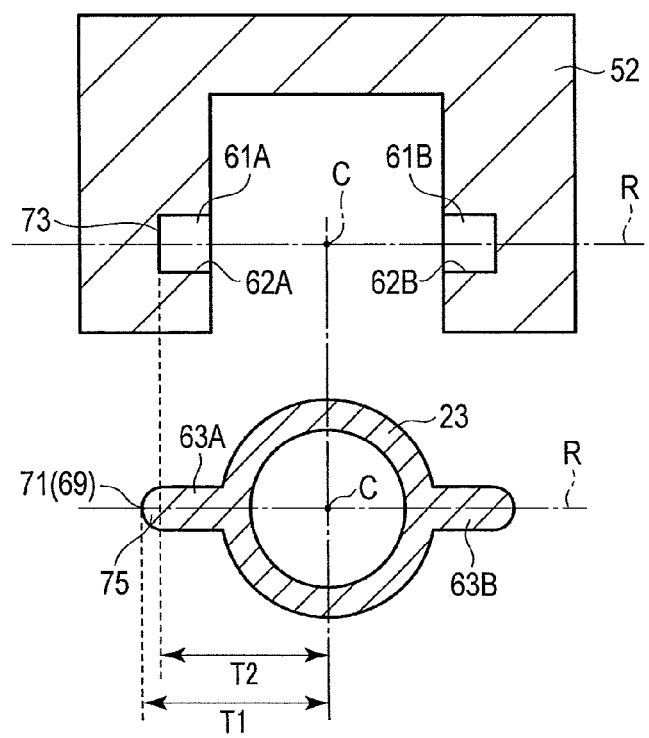
F I G. 9

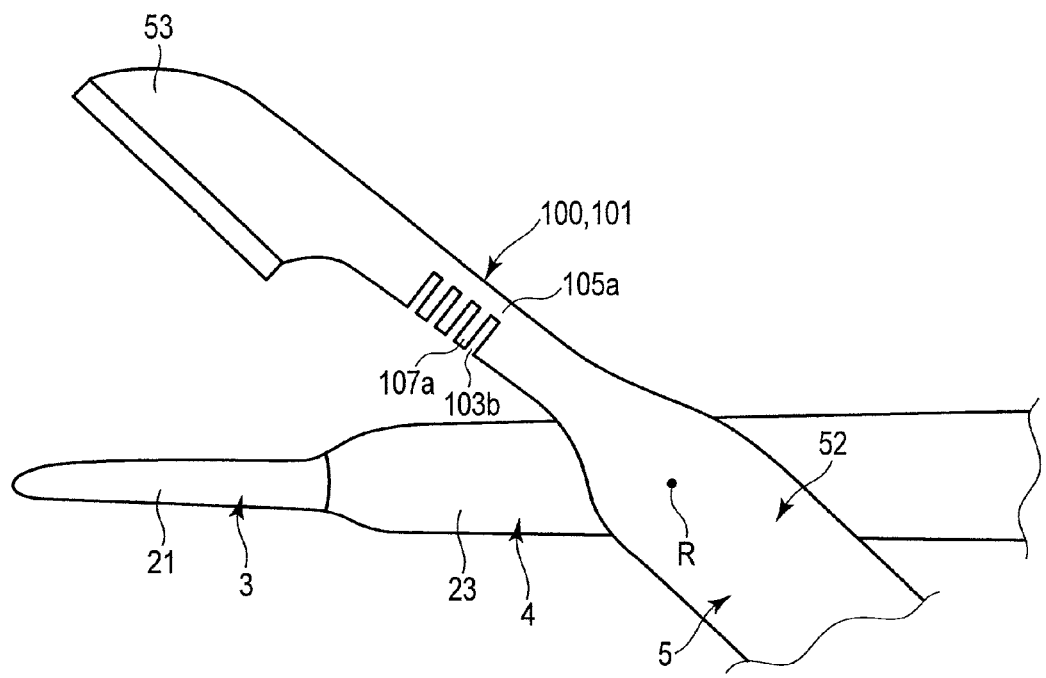
F I G. 11A
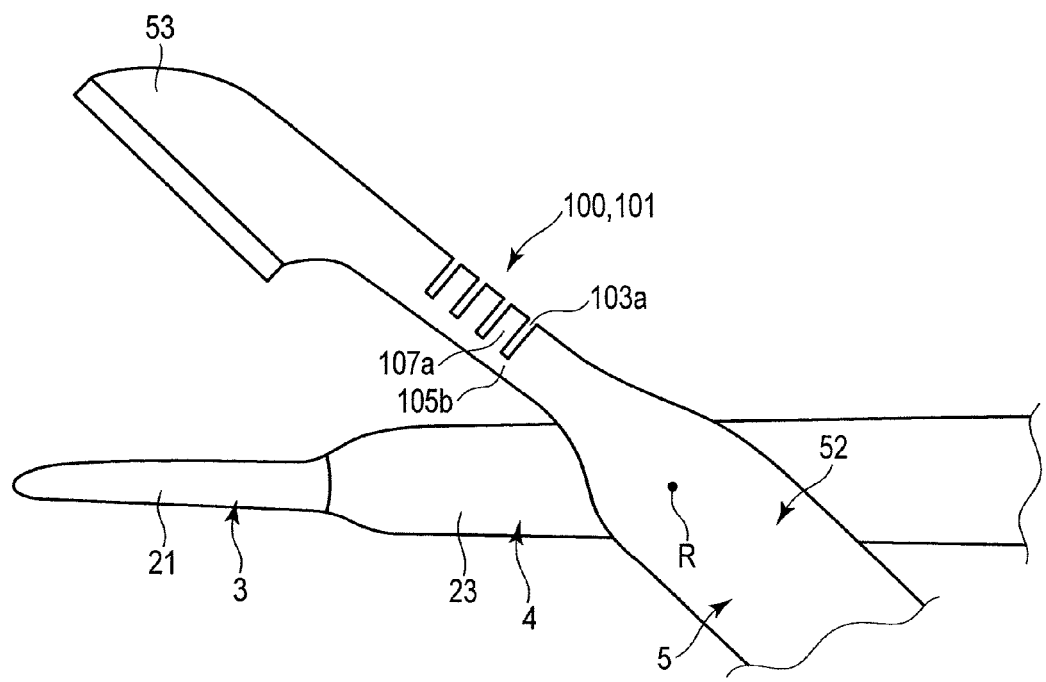
F I G. 11B

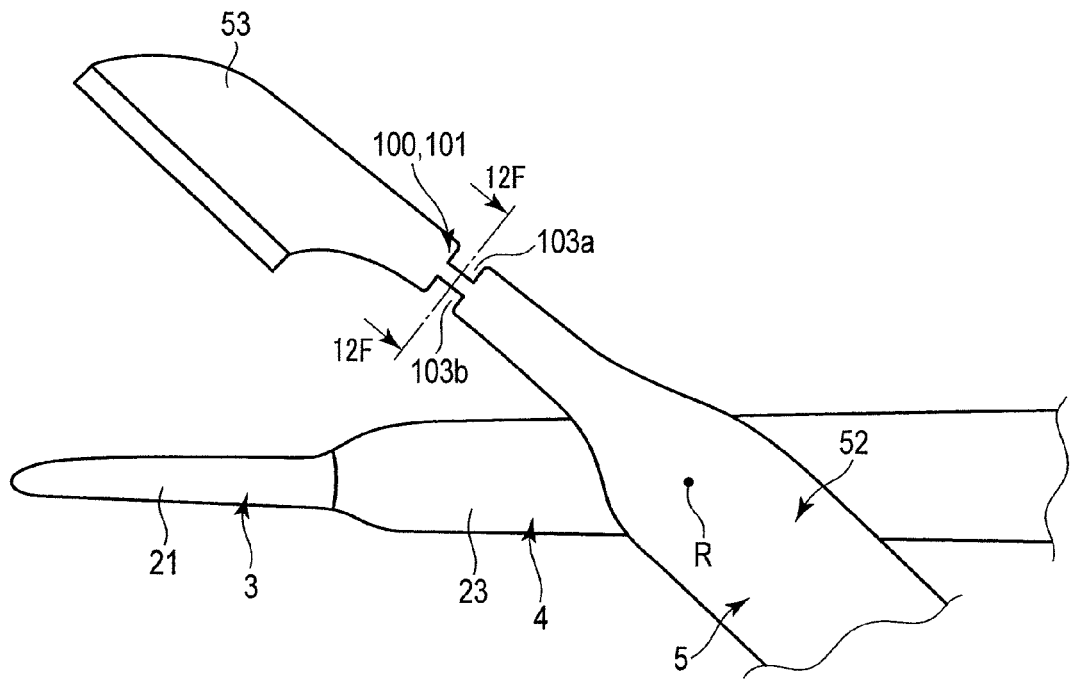
F I G. 12A
F I G. 12B
F I G. 12C

F I G. 12D
F I G. 12E
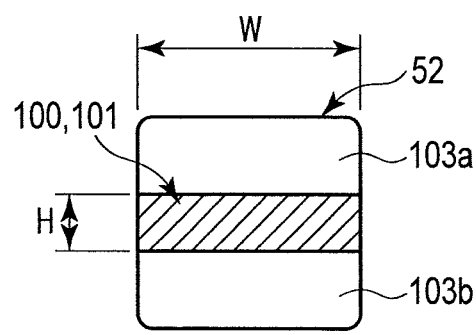
$$\frac{H}{W} < 1$$
F I G. 12F

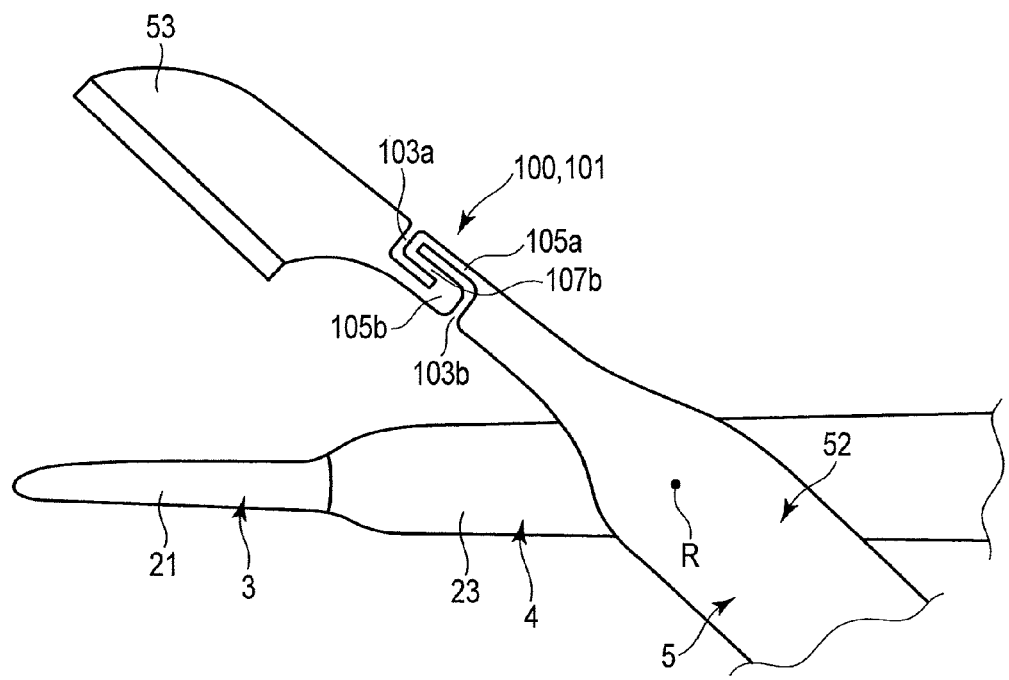
F I G. 13
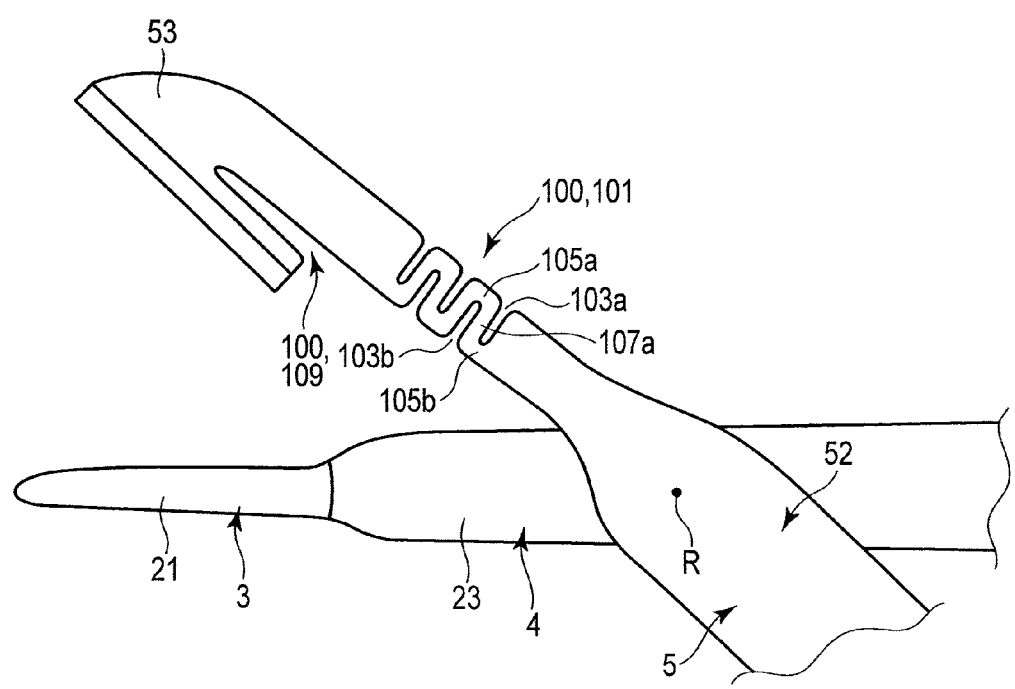
F I G. 14

ENERGY TREATMENT DEVICE

CROSS-REFERENCE TO RELATED APPLICATIONS

This application is a Continuation application of PCT Application No. PCT/JP2015/050036, filed Jan. 5, 2015 and based upon and claiming the benefit of priority from prior Japanese Patent Application No. 2014-006108, filed Jan. 16, 2014, the entire contents of all of which are incorporated herein by reference.

BACKGROUND OF THE INVENTION

1. Field of the Invention

The present invention relates to a forceps type of energy treatment device in which a movable handle is opened and closed to a fixed handle, thereby opening and closing a distal end portion of a jaw to a distal end portion of a probe.

2. Description of the Related Art

A general forceps type of energy treatment device has a probe, and a jaw which can open and close to the probe. A distal end portion of the jaw closes to a distal end portion of the probe so that the distal end portion of the jaw and the distal end portion of the probe sandwich a treatment target such as a living tissue therebetween to grasp the treatment object. The distal end portion of the jaw is opened to the distal end portion of the probe so that the distal end portion of the jaw and the distal end portion of the probe are pushed into, for example, the treatment target and to expand and peel off the treatment target.

The energy treatment device which performs a grasping operation and a peeling operation described above is disclosed in, for example, Japanese Patent No. 4727575.

BRIEF SUMMARY OF THE INVENTION

An aspect of an energy treatment device of the present invention includes a probe which extends along a longitudinal axis; a sheath unit into which the probe is inserted so that a distal end portion of the probe protrudes from a distal end of the sheath; a fixed handle which is provided in a proximal end portion of the sheath unit; a movable handle unit which is openable and closable to the fixed handle; a rotation axis which is provided in a position where the sheath unit and the movable handle unit intersect with each other and which functions as a supporting point for the movable handle unit to open and close to the fixed handle; a jaw which is provided in a distal end portion of the movable handle unit and which opens and closes to the distal end portion of the probe in accordance with the opening and closing of the movable handle unit; and a thickness-reduced portion which is one part of the jaw and which is provided between the rotation axis and a distal end of the jaw, the thickness-reduced portion flexing in response to a reaction force when one part of the jaw receives the reaction force from a treatment target due to the opening and closing of the movable handle unit to the treatment target, the thickness reduced portion preventing the deformation of the other parts of the jaw by flexing.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of a medical treatment apparatus according to a first embodiment of the present invention;

FIG. 8 is a schematic sectional view showing the configurations of a first slot defining portion and a first protrusion portion of an electric contact unit according to the first embodiment;

FIG. 9 is a schematic sectional view showing the sheath and the jaw in a situation where the jaw is not attached to the sheath according to the first embodiment;

FIG. 11A is a diagram showing a configuration of the acceleration portion according to a first modification of the first embodiment;

FIG. 11B is a diagram showing a configuration of the acceleration portion according to a second modification of the first embodiment;

FIG. 12A is a diagram showing a configuration of the acceleration portion according to a second embodiment;

FIG. 12B is a diagram showing one example of a section of the acceleration portion;

FIG. 12C is a diagram showing one example of the section of the acceleration portion;

FIG. 12D is a diagram showing one example of the section of the acceleration portion;

FIG. 12E is a diagram showing one example of the section of the acceleration portion;

FIG. 12F is a sectional view along the 12F-12F line shown in FIG. 12A;

FIG. 13 is a diagram showing a configuration of the acceleration portion according to a third embodiment;

FIG. 14 is a diagram showing a configuration of the acceleration portion according to a fourth embodiment;

DETAILED DESCRIPTION OF THE INVENTION

Hereinafter, embodiments of the present invention will be described in detail with reference to the drawings.

First Embodiment

[Configuration]

Figure 10A:
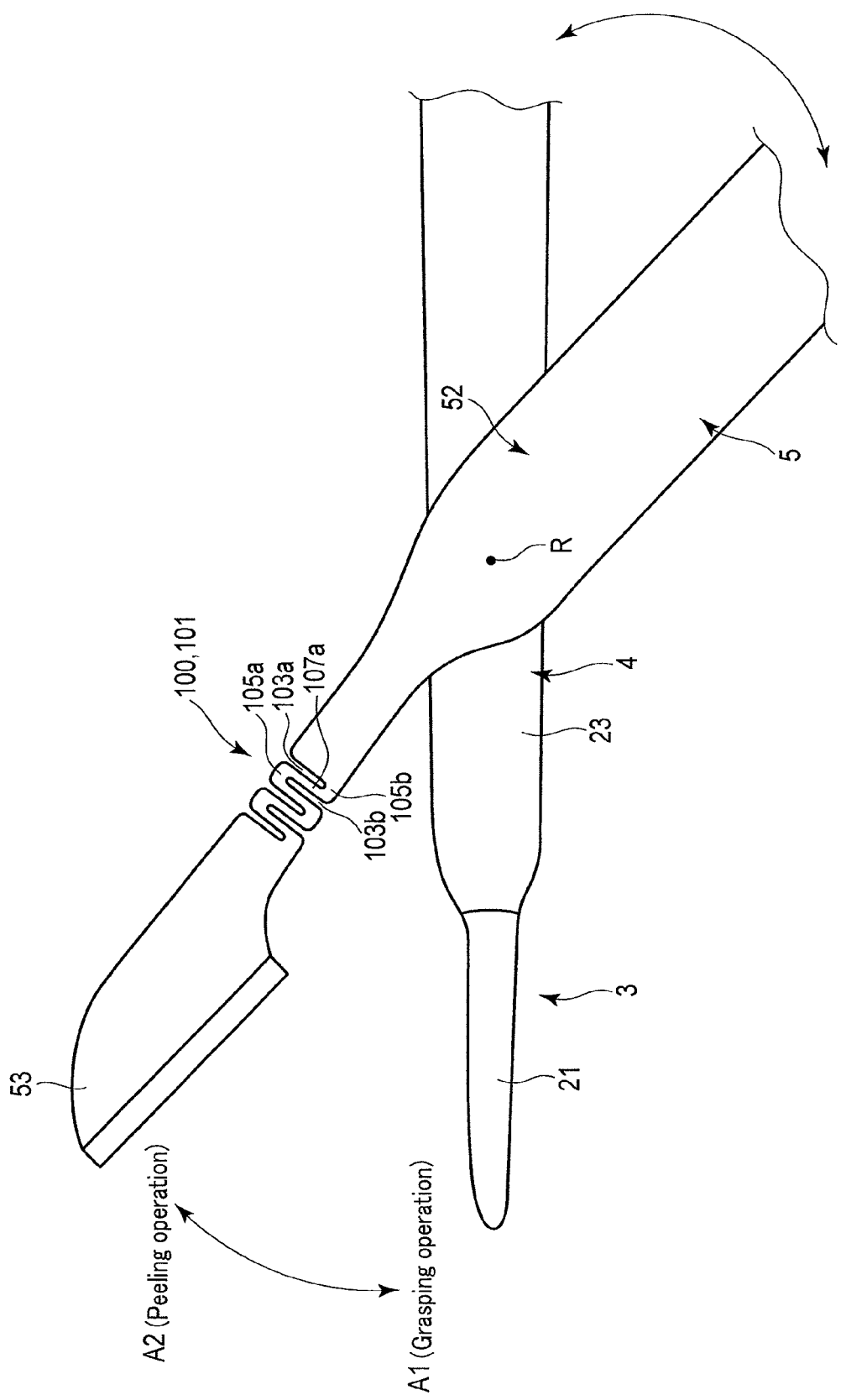
FIG. 10A is a diagram showing a configuration of an acceleration portion according to the first embodiment.

The first embodiment is described with reference to FIG. 1, FIG. 2, FIG. 3, FIG. 4, FIG. 5, FIG. 6, FIG. 7, FIG. 8, FIG. 9, FIG. 10A, FIG. 10B, and FIG. 10C. In some of the drawings, some components are not shown for clarification of diagrammatic representation. For example, the position of a second electrode portion 53 to a first electrode portion 21 in FIG. 10A is shown upside down compared to the position shown in FIG. 1 for clarification of diagrammatic representation.

[Medical Treatment Apparatus 1]

Figure 10B:
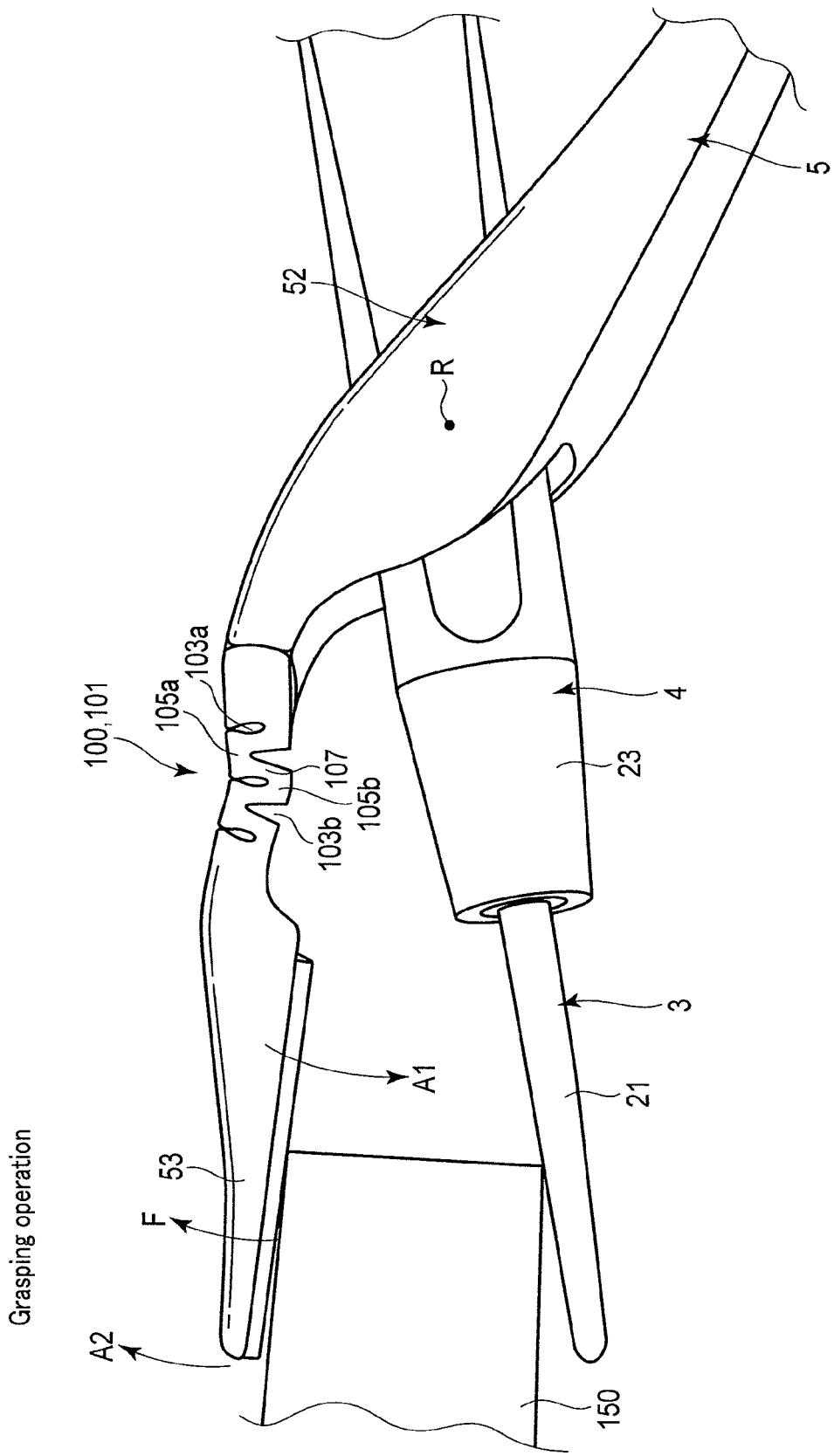
FIG. 10B is a diagram showing a function of the acceleration portion in a grasping operation.

A medical treatment apparatus 1 shown in FIG. 1 sandwiches a treatment object such as a biological tissue to grasp the treatment object by the first electrode portion. 21 located at a distal end portion of a probe 3 and the second electrode portion 53 located at a distal end portion of a later-described jaw 52 which are provided in a later-described energy treatment device (hereinafter, treatment device 10). As shown in FIG. 10B, grasping is performed when the second electrode portion 53 is closed (brought close) to the first electrode portion 21. The medical treatment apparatus 1 is capable of treating the grasped treatment target by energy such as ultrasonic waves, high-frequency waves, heat or the like. This medical treatment apparatus 1 is a grasping treatment apparatus. The medical treatment apparatus 1 according to the present embodiment is also used as a bipolar treatment apparatus which conducts a treatment by a high-frequency current by using the distal end portion of the probe 3 and the jaw 52 as electrodes. The medical treatment apparatus 1 is also used as an ultrasonic treatment apparatus that treats by ultrasonic vibration.

Figure 10C:
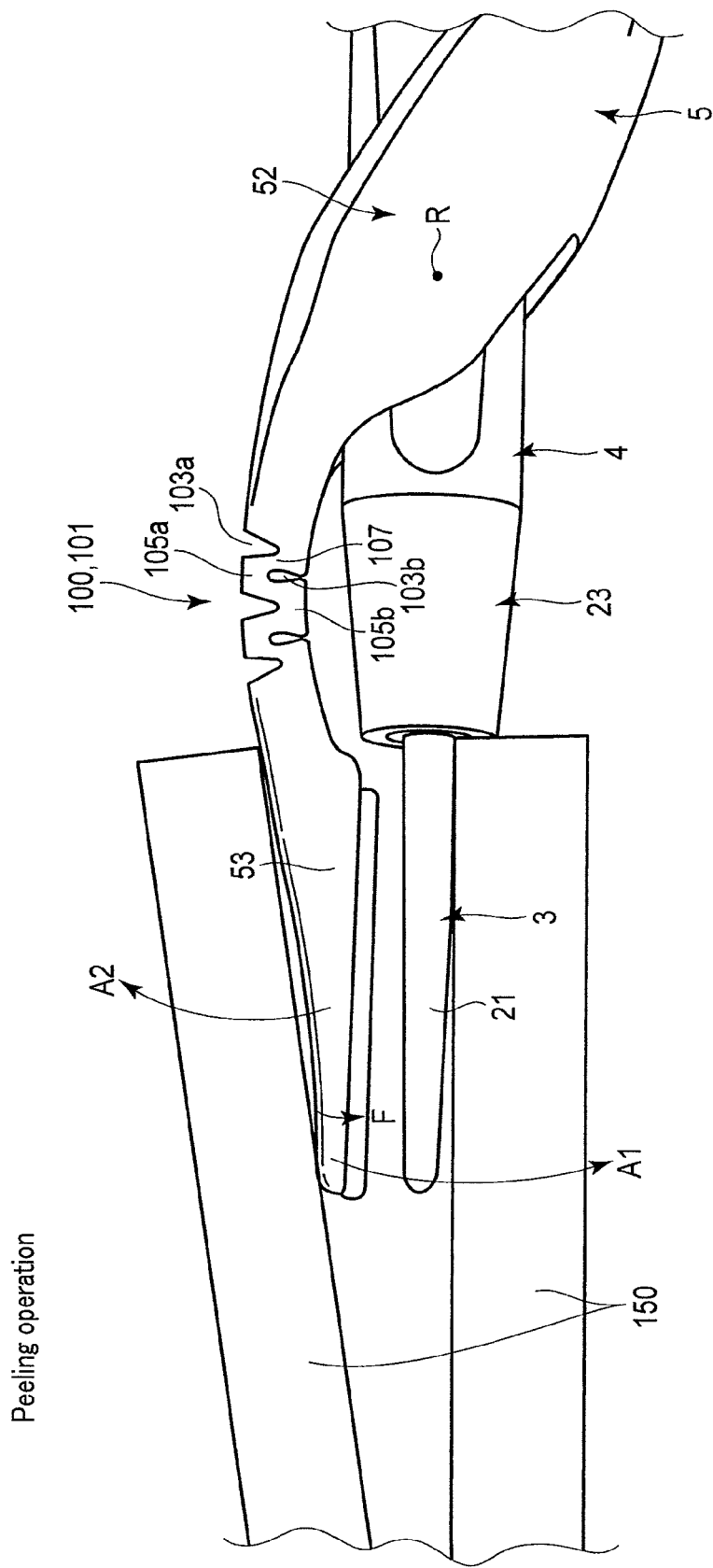
FIG. 10C is a diagram showing a function of the acceleration portion in a peeling operation.

The medical treatment apparatus 1 peels off the treatment target by the distal end portion of the probe 3 and the jaw 52 which are pushed into the treatment object. As shown in FIG. 10C, peeling is performed when the second electrode portion 53 opens (comes away) from the first electrode portion 21.

As shown in FIG. 1, the medical treatment apparatus 1 has a power supply unit 7 which functions as a supply unit to supply electric power for energy, and the treatment device 10 which treats the treatment target by energy supplied from the power supply unit 7.

[Power Supply Unit 7]

As shown in FIG. 1, the power supply unit 7 has an ultrasonic control unit 8 which controls a current for ultrasonic vibration, and a hi frequency current control unit 9 which controls a current for high-frequency waves. The power supply unit 7 further has a cable 6 which is electrically connected to the ultrasonic control unit 8 and the treatment device 10 and which is electrically connected to the high-frequency current control unit 9 and the treatment device 10. One end of the cable 6 is connected to the power supply unit 7, and the other end of the cable 6 is connected to a proximal end of a later-described transducer case 11.

[Treatment Device 10]

As shown in FIG. 1, the treatment device 10 has a transducer unit 2, the probe 3, a sheath unit 4, and a movable handle unit 5. The transducer unit 2, the probe 3, and the sheath unit 4 are on a fixed side, and the movable handle unit 5 is on a movable side which is rotatably movable to the fixed side.

[Transducer Unit 2]

Figure 2:
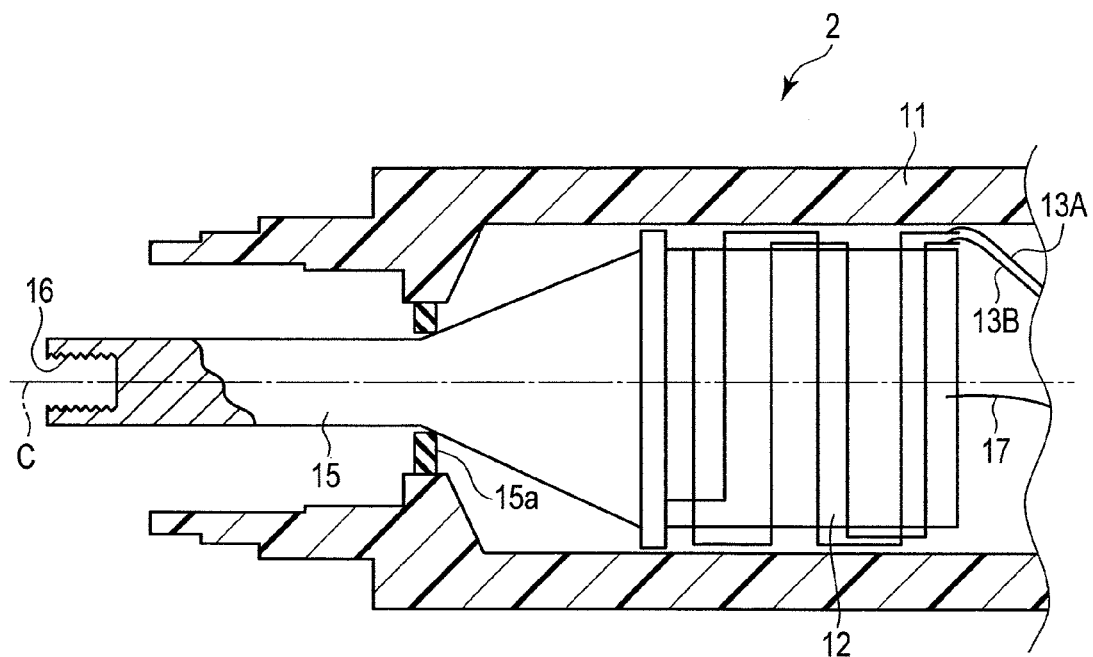
FIG. 2 is a sectional view showing a configuration of a transducer unit.

As shown in FIG. 1 and FIG. 2, the transducer unit 2 has the transducer case 11. As described above, the proximal end of the transducer case 11 is connected to the end portion of the cable 6.

As shown in FIG. 2, the transducer unit 2 has an ultrasonic transducer 12 which is provided inside the transducer case 11 and which has a piezoelectric element to convert the current supplied from the ultrasonic control unit 8 into ultrasonic vibration.

The ultrasonic transducer 12 is connected to one end of each of electric signal lines 13A and 13B. The electric signal lines 13A and 13B are provided inside the cable 6. The other end of each of the electric signal lines 13A and 13B is connected to the ultrasonic control unit 8 of the power supply unit 7. When the current is supplied to the ultrasonic transducer 12 from the ultrasonic control unit 8 via the electric signal lines 13A and 13B, ultrasonic vibration is generated in the ultrasonic transducer 12.

The ultrasonic transducer 12 is connected to one end of an electric signal line 17 separately from the electric signal lines 13A and 13B. The electric signal line 17 is provided inside the cable 6. The other end of the electric signal line 17 is connected to the high-frequency current control unit 9 of the power supply unit 7.

The electric signal lines 13A, 13B, and 17 are included in the cable 6.

As shown in FIG. 2, the transducer unit 2 further has a horn 15 which is coupled to a distal end of the ultrasonic transducer 12 to be located at the distal end of the ultrasonic transducer 12 and which increases the amplitude of the ultrasonic vibration generated in the ultrasonic transducer 12.

The horn 15 is attached to the transducer case 11 via an insulating member 15a. The horn 15 is electrically insulated from the transducer case 11 by the insulating member 15a. The horn 15 has an internal thread portion 16 formed at a distal end portion of the horn 15.

[Probe 3]

Figure 3:
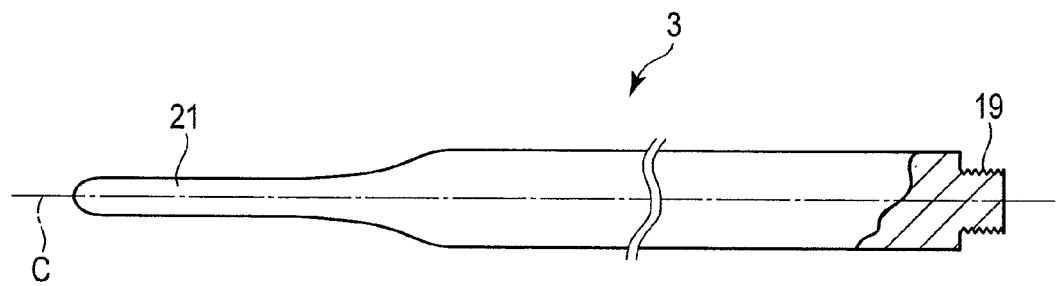
FIG. 3 is a side view including a partial cross section of a probe.

As shown in FIG. 3, the probe 3 extends along a longitudinal axis C. The probe 3 has a columnar shape. The probe 3 has an external thread portion 19 which is formed at a proximal end portion of the probe 3 and which is tightened to the internal thread portion 16 of the horn 15.

The probe 3 is attached to the horn 15 by the tightening of the threads. As a result, the ultrasonic vibration generated in the ultrasonic transducer 12 is transmitted to the distal end of the probe 3 via the horn 15 and the probe 3. That is, the ultrasonic vibration is transmitted from the proximal end of the probe 3 to its distal end portion. It is to be noted that the ultrasonic vibration is a vertical vibration in which a transmitting direction of the vibration matches a vibrating direction.

When the probe 3 is attached to the horn 15, a probe-side current path of the high-frequency current is formed from the high-frequency current control unit 9 to the distal end portion of the probe 3 through the electric signal line 17, the ultrasonic transducer 12, and the horn 15. The probe 3 has the first electrode portion 21 formed at the distal end portion of the probe 3. That is, the high-frequency current is transmitted by the probe-side current path between the high-frequency current control unit 9 and the first electrode portion 21 along the longitudinal axis C.

[Sheath Unit 4]

As shown in FIG. 1, the sheath unit 4 extends along the longitudinal axis C. The sheath unit 4 has a fixed handle 22, and a sheath 23 which is attached to the distal end of the fixed handle 22.

Figure 4:
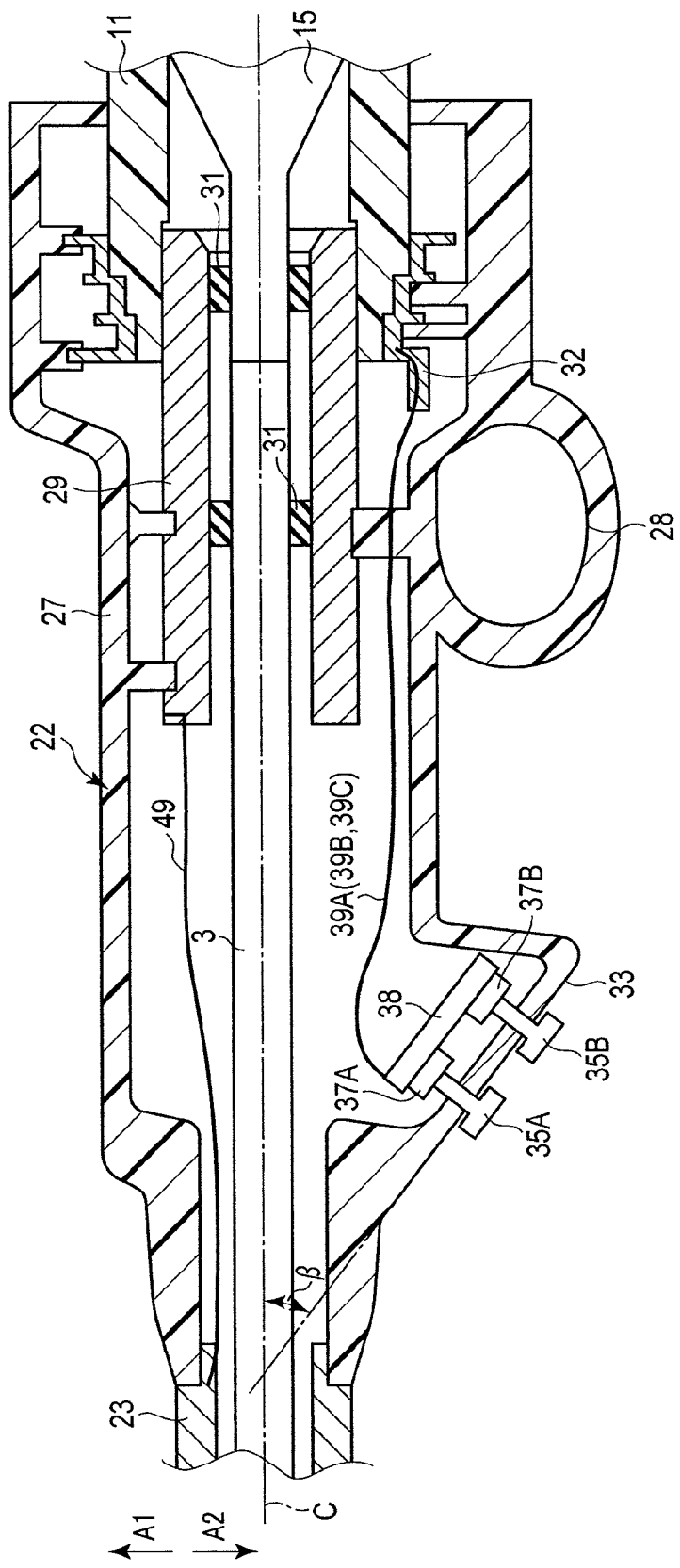
FIG. 4 is a schematic sectional view showing an inner configuration of a fixed handle.

As shown in FIG. 1 and FIG. 4, the fixed handle 22 has a handle casing 27 which functions as an exterior portion. The handle casing 27 has a fixed handle ring 28 which is provided in a part of the handle casing 27 on a later-described second open-close direction side and which functions as a fixed-side finger putting portion.

As shown in FIG. 4, in the fixed handle 22, the handle casing 27 has a cylindrical member 29 which is provided inside the handle casing 27 and which is fixed to the handle casing 27. The proximal end of the probe 3 extends into the cylindrical member 29. As described above, the probe 3 is attached to the horn 15 inside the cylindrical member 29. The cylindrical member 29 supports the probe 3 and the horn 15 via an insulating member 31. Thus, the probe 3 and the horn 15 are prevented from coming in contact with the cylindrical member 29, and the probe 3 and the horn 15 are electrically insulated from the cylindrical member 29.

An electric connection ring 32 is provided on an outer circumferential direction side of the cylindrical member 29. The electric connection ring 32 is fixedly provided in the handle casing 27. A distal end portion of the transducer case 11 is engaged in between the cylindrical member 29 and the electric connection ring 32. The distal end portion of the transducer case 11 is engaged in between the cylindrical member 29 and the electric connection ring 32, whereby the transducer case 11 is coupled to the fixed handle 22 (the sheath unit 4 and the handle casing 27). In a state where the transducer case 11 is coupled to the fixed handle 22, an outer circumferential portion of the distal end portion of the transducer case 11 is in contact with the electric connection ring 32, and an inner circumferential portion of the distal end portion of the transducer case 11 is in contact with the cylindrical member 29.

As shown in FIG. 1 and FIG. 4, the handle casing 27 has an inclined flat plane 33 which is provided in a part on the side of the second open-close direction (the direction of an arrow A2 shown in FIG. 1 and FIG. 4) of the handle casing 27 (the fixed handle 22) and which is inclined to the longitudinal axis C. This inclined flat plane 33 is provided on a distal end direction side to the fixed handle ring 28. The inclined flat plane 33 is positioned on a proximal end direction side as the inclined flat surface is away from a first direction (a direction of an arrow A1 shown in FIG. 1 and FIG. 4) toward the second direction. In other words, the inclined flat plane 33 is upwardly inclined from the distal end direction side of the handle casing 27 toward a proximal end direction side. Thus, the angle between the inclined flat plane 33 and the longitudinal axis C has an acute angle β.

As shown in FIG. 1 and FIG. 4, the handle casing 27 has input buttons 35A and 35B which are two operation input portions provided in the inclined flat plane 33. If the input buttons 35A and 35B are pushed, an operator's operation is input. The press directions of input buttons 35A and 35B are perpendicular to the inclined flat plane 33.

As shown in FIG. 1 and FIG. 4, the handle casing 27 has switch portions 37A and 37B and an electric circuit substrate 38 which are provided on an inner circumferential direction side of the inclined flat plane 33. Opening and closing states of the switch portion 37A are switched by the input operation in the input button 35A. Similarly, Opening and closing states of the switch portion 37B are switched by the input operation in the input button 35B.

Figure 5:
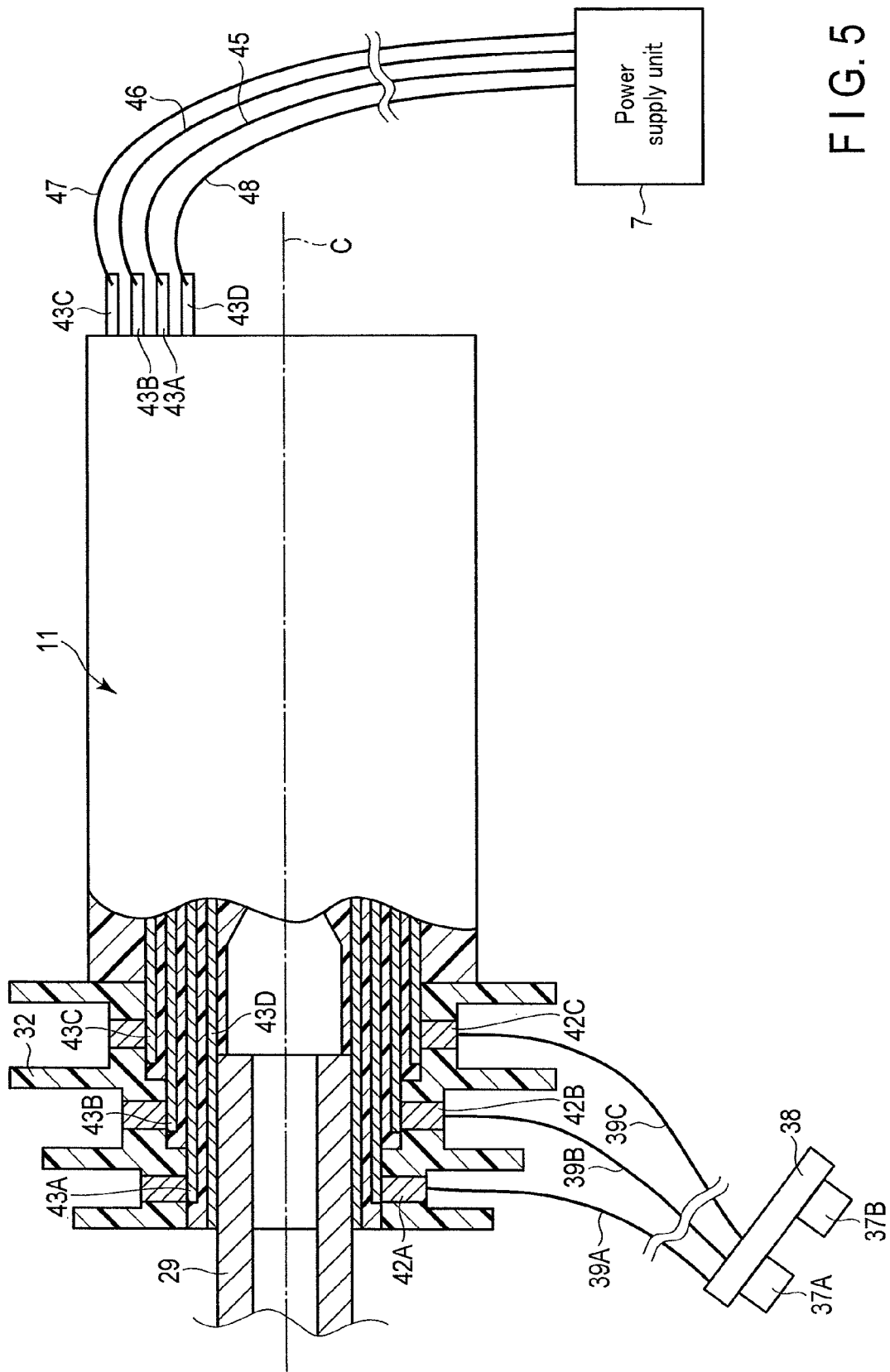
FIG. 5 is a schematic view showing an electric connection state in a transducer case, a cylindrical member, and an electric connection ring.

FIG. 5 is a diagram schematically showing the electric connection state of the transducer case 11, the cylindrical member 29, and the electric connection ring 32. As shown in FIG. 4 and FIG. 5, the handle casing 27 has three electric signal lines 39A, 393, and 39C which are provided in the handle casing 27. The electric signal line 39A is electrically connected to the switch portion 37A via the electric circuit substrate 38. The electric signal line 393 is electrically connected to the switch portion 37B via the electric circuit substrate 38. The electric signal line 39C is electrically connected to the switch portion 37A and the switch portion 37B via the electric circuit substrate 38. The electric signal line 39C is a common line shared as a ground line of the switch portion 37A and the switch portion 37B.

As shown in FIG. 5, the electric connection ring 32 has a first electric connection portion 42A, a second electric connection portion 42B, and a third electric connection portion 42C. The first electric connection portion 42A is electrically insulated from the second electric connection portion 42B, the second electric connection portion 42B is electrically insulated from the third electric connection portion 42C, the first electric connection portion 42A is electrically insulated from the third electric connection portion 42C. The electric signal line 39A is connected to the first electric connection portion 42A. The electric signal line 39B is connected to the second electric connection portion 42B. The electric signal line 39C is connected to the third electric connection portion 42C.

As shown in FIG. 5, the transducer case 11 has a first electrically conductive portion 43A, a second electrically conductive portion 43B, and a third electrically conductive portion 43C. The first electrically conductive portion 43A, the second electrically conductive portion 43B, and the third electrically conductive portion 43C extend along the longitudinal axis C. The first electrically conductive portion 43A is electrically insulated from the second electrically conductive portion 43B, the second electrically conductive portion 43B is electrically insulated from the third electrically conductive portion 43C, the first electrically conductive portion 43A is electrically insulated from the third electrically conductive portion 43C. In the state where the transducer case 11 is coupled to the fixed handle 22 (the sheath unit 4), a distal end portion of the first electrically conductive portion 43A is only in electric contact with the first electric connection portion 42A of the electric connection ring 32. Similarly, a distal end portion of the second electrically conductive portion 43B is only in electric contact with the second electric connection portion 42B of the electric connection ring 32. A distal end portion of the third electrically conductive portion 43C is only in electric contact with the third electric connection portion 42C of the electric connection ring 32.

As shown in FIG. 5, a proximal end portion of the first electrically conductive portion 43A is connected to one end of an electric signal line 45. A proximal end portion of the second electrically conductive portion 43B is connected to one end of an electric signal line 46. A proximal end portion of the third electrically conductive portion 43C is connected to one end of an electric signal line 47. The electric signal lines 45, 46, and 47 are provided inside the cable 6. The other ends of the electric signal lines 45, 46, and 47 are connected to the power supply unit 7.

As described above, a first electric signal path is formed from the switch portion 37A to the power supply unit 7 through the electric signal line 39A, the first electric connection portion 42A, the first electrically conductive portion 43A, and the electric signal line 45. A second electric signal path is formed from the switch portion 37B to the power supply unit 7 through the electric signal line 39B, the second electric connection portion 42B, the second electrically conductive portion 43B, and the electric signal line 46. Moreover, a ground path is formed from the switch portion 37A and the switch portion 37B to the power supply unit 7 through the electric signal line 39C, the third electric connection portion 42C, the third electrically conductive portion 43C, and the electric signal line 47.

If the input button 35A is pressed, the switch portion 37A is a closed state, and the first electric signal path is electrically connected to the ground path by the switch portion 37A. As a result, an electric signal is transmitted to the power supply unit 7 from the switch portion 37A. For example, the state is then switched so that a current is supplied to the ultrasonic transducer 12 from the ultrasonic control unit 8 via the electric signal lines 13A and 13B, ultrasonic vibration is generated in the ultrasonic transducer 12, and the high-frequency current is output from the high-frequency current control unit 9 at the same time.

If the input button 35B is pushed, the switch portion 37B is a closed state, and the second electric signal path is electrically connected to the ground path by the switch portion 37B. As a result, an electric signal is transmitted to the power supply unit 7 from the switch portion 37B. For example, the state is then switched so that the high-frequency current is output from the high-frequency current control unit 9 alone, and no ultrasonic vibration is generated.

As shown in FIG. 5, the transducer case 11 further has a fourth electrically conductive portion 43D which extends along the longitudinal axis C. The first electrically conductive portion 43A, the second electrically conductive portion 43B, and the third electrically conductive portion 43C are all electrically insulated from the fourth electrically conductive portion 43D. A proximal end portion of the fourth electrically conductive portion 43D is connected to one end of an electric signal line 48. The electric signal line 48 is provided inside the cable 6. The other end of the electric signal line 48 is connected to the high-frequency current control unit 9 of the power supply unit 7. In the state where the transducer case 11 is coupled to the fixed handle 22 (the sheath unit 4), a distal end portion of the fourth electrically conductive portion 43D is only in electric contact with the cylindrical member 29.

As shown in FIG. 4, the cylindrical member 29 is connected to one end of an electric signal line 49. The other end of the electric signal line 49 is connected to the sheath 23. In this way, the high-frequency current is transmitted between the high-frequency current control unit 9 and the sheath 23 via the electric signal line 48, the fourth electrically conductive portion 43D, the cylindrical member 29, and the electric signal line 49.

Figure 6:
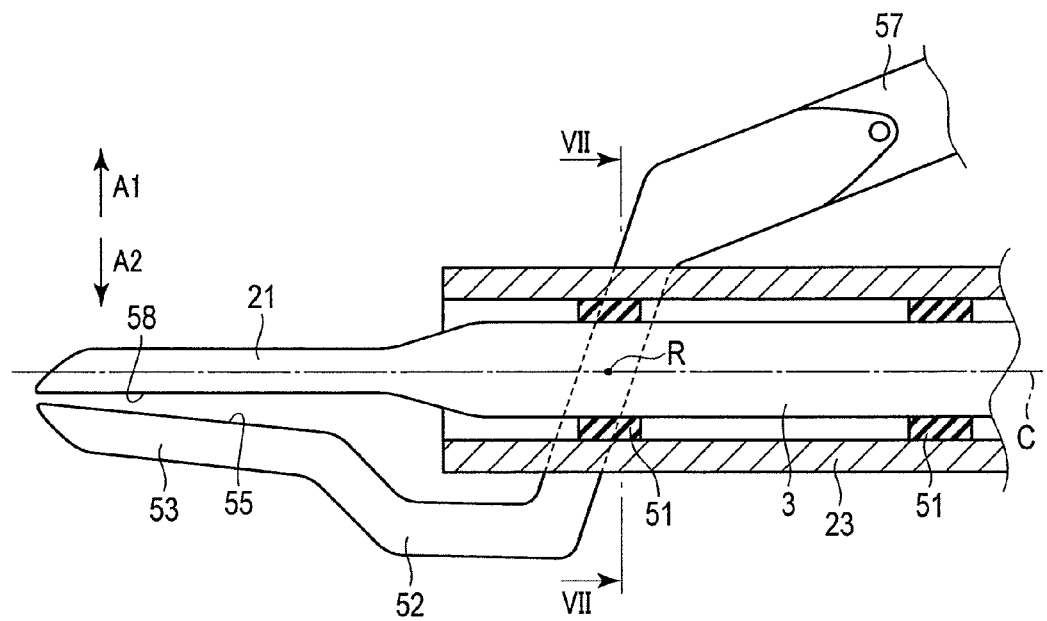
FIG. 6 is a schematic sectional view showing how the probe is inserted into a sheath according to the first embodiment.

As shown in FIG. 4 and FIG. 6, the sheath 23 is provided on the outer circumferential direction side to the probe 3. The probe 3 is inserted into the sheath 23 so that the first electrode portion 21 which functions as the distal end portion of the probe 3 protrudes from a distal end of the sheath 23.

As shown in FIG. 6, the sheath 23 has a support member 51 which is provided between the probe 3 and the sheath 23 in a radial direction of the sheath 23 and which supports the probe 3. The support member 51 is made of an insulating material. The support member 51 prevents the contact between the probe 3 and the sheath 23, and electrically insulates the probe 3 from the sheath 23. In the present embodiment, the support member 51 is disposed at the node position of ultrasonic vibration. This more effectively prevents the contact between the probe 3 and the sheath 23. One or more support members 51 may be provided, and at least one support member 51 has only to be provided.

[Movable Handle Unit 5]

As shown in FIG. 1 and FIG. 10A, the movable handle unit 5 can open and close to the fixed side including the probe 3 and the sheath unit 4 for a treatment operation to treat the treatment target. The movable handle unit 5 has a movable handle 25 which is provided in a proximal end portion of the movable handle unit and which functions as a force application point in the treatment operation. The movable handle 25 can open and close to the fixed handle 22 around a later-described rotation axis R as a center which perpendicular to the longitudinal axis C in an open-close direction along the circumference of the rotation axis. The movable handle 25 has a movable handle ring 26 which functions as a movable-side finger placing portion. The movable handle 25 can open and close to the fixed handle 22 in a first open-close direction (first direction) perpendicular to the longitudinal axis C indicated in the arrow A1 direction in FIG. 1, and in a second open-close direction (second direction) which is a direction opposite to the first open-close direction indicated in the arrow A2 direction in FIG. 1. The movable handle 25 is located closer to the first open-close direction side to the fixed handle 22. An axis L1 of the movable handle 25 is inclined to have an acute angle α with the longitudinal axis C.

The movable handle unit 5 further has the jaw 52 which is rotatably attached to the distal end portion of the sheath 23, and an relay member 57 provided between the movable handle 25 and the jaw 52. When the jaw 52 is attached to the sheath 23, the movable handle unit 5 is coupled to the sheath unit 4. The jaw 52 has the second electrode portion 53 which is provided in a distal end portion of the movable handle unit 5 and which functions as a jaw distal end portion that functions as an action point in the treatment operation. The jaw 52 is attached to the distal end portion of the sheath 23 so that the jaw 52 is rotatable around the rotation axis R as the center. The jaw 52 rotates around the rotation axis R as the center in accordance with the opening and closing of the movable handle 25 and can thereby open and close in an open-close direction which intersects with, more specifically, is perpendicular to the longitudinal axis direction and the rotation axis direction to the first electrode portion 21 which functions as the distal end portion of the probe 3. The jaw 52 can open and close to the first electrode portion 21 which is provided at the distal end portion of the probe 3. The jaw 52 has the second electrode portion 53 which is located on a second open-close direction (the direction of the arrow A2 shown in FIG. 1 and FIG. 6) to the first electrode portion 21 of the probe 3. The second electrode portion 53 is electrically connected to the sheath 23. The second electrode portion 53 has a probe facing portion 55 which is provided in a part of an outer surface of the second electrode portion 53 (jaw 52) on the first open-close direction (the direction of an arrow A1 shown in FIG. 1 and FIG. 6) side and which faces the first electrode portion 21. Similarly, the first electrode portion 21 has a jaw facing portion 58 which is provided in a part of an outer surface of the first electrode portion 21 on the second open-close direction (the direction of an arrow A2 shown in FIG. 1 and FIG. 6) side and which faces the second electrode portion 53.

The movable handle unit 5 has the rotation axis R which is provided at a coupling portion of the movable handle unit 5 and the sheath 23 and which functions as a rotation center. The rotation axis R intersects with the longitudinal axis C, and is provided perpendicularly to the longitudinal axis C and perpendicularly to the first open-close direction and the second open-close direction. The movable handle unit 5 rotates around this rotation axis.

Thus, the movable handle 25 moves in the first open-close direction, and the movable handle 25 performs an opening operation to the fixed handle 22, whereby the jaw 52 moves in the second open-close direction. In consequence, the jaw 52 is at an opening position to the first electrode portion 21.

The movable handle 25 moves in the second open-close direction, and the movable handle 25 performs a closing operation to the fixed handle 22, whereby the jaw 52 moves in the first open-close direction. In consequence, the jaw 52 is at a closing position to the first electrode portion 21.

That is, the jaw 52 performs the open-close operations to the first electrode portion 21 to the opening position and the closing position by rotating to the sheath 23 around the rotation axis R as the center.

As described above, the second electrode portion 53 is electrically connected to the sheath 23. Thus, the high-frequency current is transmitted between the sheath 23 and the second electrode portion 53. The high-frequency current is transmitted between the high-frequency current control unit 9 and the sheath 23 via the electric signal line 48, the fourth electrically conductive portion 43D, and the electric signal line 49. Therefore, a jaw-side current path is formed from the high-frequency current control unit 9 to the second electrode portion 53 of the jaw 52 through the electric signal line 48, the fourth electrically conductive portion 43D, the electric signal line 49, and the sheath 23. That is, the high-frequency current is transmitted between the high-frequency current control unit 9 and the second electrode portion 53 by the jaw-side current path.

An outer surface of the sheath 23 and an outer surface of a part of the jaw 52 other than the probe facing portion 55 are, for example, coated for insulation. This prevents an electric shock even when, for example, the hand of the operator has touched the outer surface of the sheath 23 or the outer surface of the jaw 52. The relay member 57 provided between the jaw 52 and the movable handle 25 is made of an insulating material. This prevents the transmission of the high-frequency current from the jaw 52 to the movable handle 25.

[Electric Contact Unit 60]

Figure 7:
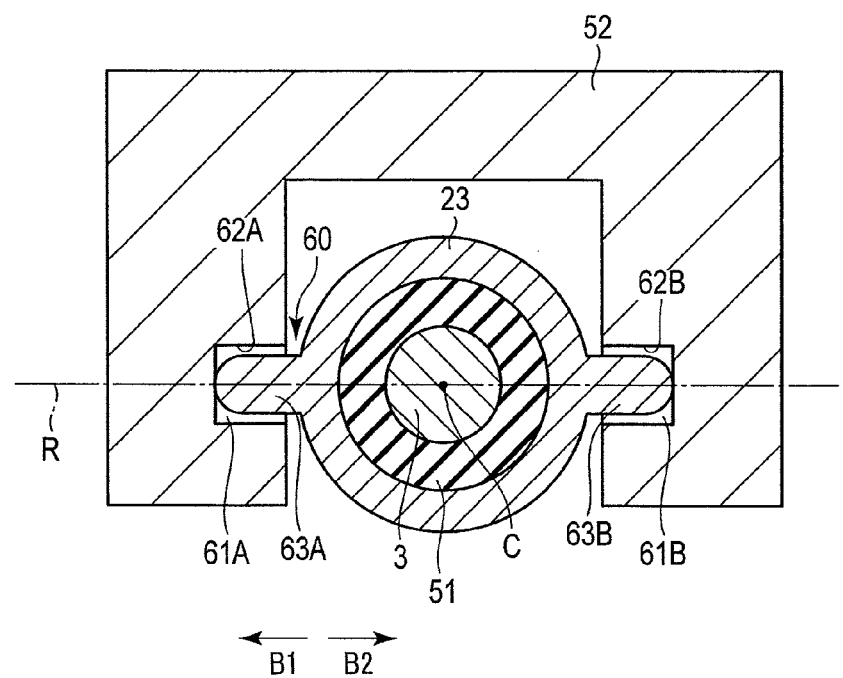
FIG. 7 is a sectional view along the VII-VII line shown in FIG. 6.

As shown in FIG. 7, the treatment device 10 further has an electric contact unit 60 which is provided between the sheath 23 and the jaw 52 and which holds the state in which the high-frequency current is always transmitted between the sheath 23 and the second electrode portion 53 of the jaw 52. This electric contact unit 60 functions as a coupling portion to couple the sheath 23 with the jaw 52 to rotate the jaw 52 to the sheath 23 around the rotation axis R as the center. The electric contact unit 60 has a first slot portion 61A and a second slot portion 61B which are depressed in the jaw 52 along the rotation axis R in the outer circumferential direction. The first slot portion 61A is depressed in a first rotation axis direction (the direction of an arrow B1 shown in FIG. 7) parallel to the rotation axis R. The second slot portion 61B is depressed in a second rotation axis direction (the direction of an arrow B2 shown in FIG. 7) which is a direction opposite to the first rotation axis direction. The first slot portion 61A is defined by a first slot defining portion 62A, and the second slot portion 61B is defined by a second slot defining portion 62B.

The electric contact unit 60 has a first protrusion portion 63A and a second protrusion portion 63B which protrude in the outer circumferential direction along the rotation axis R in an outer circumferential portion of the sheath 23. The first protrusion portion 63A protrudes in the first rotation axis direction, and the second protrusion portion 63B protrudes in the second rotation axis direction. The first protrusion portion 63A is inserted to the first slot portion 61A, and the second protrusion portion 63B is inserted to the second slot portion 61B.

FIG. 8 is a diagram showing the configurations of the first slot defining portion 62A and the first protrusion portion 63A. Although only the first slot defining portion 62A and the first protrusion portion 63A are described below, the configuration of the second slot defining portion 62B is similar to the configuration of the first slot defining portion 62A, and the configuration of the second protrusion portion 63B is similar to the configuration of the first protrusion portion 63A. Therefore, the second slot defining portion 62B and the second protrusion portion 63B are not described.

As shown in FIG. 8, the first slot defining portion 62A has a slot side surface 65 and a slot bottom surface 67. The first protrusion portion 63A has a protruding end 69. The first protrusion portion 63A is inserted to the first slot portion 61A with a space portion between the first protrusion portion 63A and the slot side surface 65. A sheath-side contact portion 71 is located at the protruding end 69. That is, the sheath-side contact portion 71 is provided in the outer circumferential portion of the sheath 23. A jaw-side contact portion 73 is located on the slot bottom surface 67 of the first slot defining portion 62A of the jaw 52. That is, the jaw-side contact portion 73 is provided in an inner circumferential portion of the jaw 52. The jaw-side contact portion 73 slidably contacts the sheath-side contact portion 71. A high-frequency current is transmitted between the sheath 23 and the second electrode portion 53 of the jaw 52 by the contact between the jaw-side contact portion 73 and the sheath-side contact portion 71.

FIG. 9 is a diagram showing the sheath 23 and the jaw 52 in a situation where the jaw 52 is not attached to the sheath 23. As shown in FIG. 9, in the situation where the jaw 52 is not attached to the sheath 23, a first dimension T1 from the longitudinal axis C to the sheath-side contact portion 71 along the rotation axis R is greater than a second dimension T2 from the longitudinal axis C to the jaw-side contact portion 73 along the rotation axis R. According to this configuration, the contact between the jaw-side contact portion 73 and the sheath-side contact portion 71 is always maintained even when the space portion is provided between the first protrusion portion 63A and the slot side surface 65 of the first slot defining portion 62A. Therefore, the situation where the high-frequency current is transmitted between the sheath 23 and the second electrode portion 53 of the jaw 52 is maintained.

As shown in FIG. 8, the first protrusion portion 63A comprises a protrusion portion-side semispherical portion 75 which is semispherically provided up to the sheath-side contact portion 71 along the rotation axis R. The protrusion portion-side semispherical portion 75 is a protrusion portion-side section changing portion which decreases in sectional area perpendicular to the rotation axis R toward the protruding end 69 of the first protrusion portion 63A along the rotation axis R. The contact area of the sheath-side contact portion 71 and the jaw-side contact portion 73 is reduced by the protrusion portion-side semispherical portion 75.

[Elastic Deformation Acceleration Portion (Hereinafter, Acceleration Portion 100)]

As shown in FIG. 1, FIG. 10A, FIG. 10B, and FIG. 10C, the treatment device 10 further has an acceleration portion 100 provided in, for example, the movable handle unit 5 which is on the movable side. When the movable handle unit 5 opens and closes to the fixed side for a treatment operation such as a grasping operation and a peeling operation and the movable handle unit 5 receives a reaction force F from a treatment target 150 due to the open-close operations, the acceleration portion 100 accelerates the elastic deformation of the movable handle unit 5 in a direction in which the movable handle unit 5 has received the reaction force F. As shown in FIG. 10A, when the treatment operation has finished and the reaction force F is no longer applied to the movable handle unit 5, the acceleration portion 100 accelerates the elastic deformation of the movable handle unit 5 to the side opposite to the direction in which the movable handle unit 5 has received the reaction force F so that the movable handle unit 5 is restored to the original state showing the state before the start of the treatment operation.

[Position of Acceleration Portion 100]

As shown in FIG. 1 and FIG. 10A, for example, in an axial direction of the movable handle unit 5, the acceleration portion 100 is provided closer to the side of the second electrode portion 53 provided in the distal end portion side of the jaw 52 which functions as the action point in the treatment operation to the side of the movable handle 25 which functions as the force application point in the treatment operation.

As shown in FIG. 1 and FIG. 10A, in the above, the acceleration portion 100 is preferably provided, in the axial direction of the movable handle unit 5, between the second electrode portion 53 provided at the distal end portion of the jaw 52 which functions as the action point in the treatment operation and the rotation axis R which functions as a supporting point in the treatment operation.

In general, when the movable handle unit 5 opens and closes to the sheath unit 4 for the treatment operation, the reaction force F is applied the most to a part between the second electrode portion 53 which functions as the action point and the rotation axis R which functions as a supporting point in the axial direction of the movable handle unit 5. In particular, the reaction force F is applied more to the rotation axis R side to the second electrode portion 53 side. Thus, the most load is applied to the rotation axis R side, and the rotation axis R side needs to divert the load.

In view of this fact, as shown in FIG. 1 and FIG. 10A, the acceleration portion 100 is particularly preferably provided in the axial direction of the movable handle unit 5, closer to the rotation axis R side which functions as a supporting point in the treatment operation to the second electrode portion 53 side provided in the distal end portion side of the jaw 52 which functions as the action point in the treatment operation.

As shown in FIG. 1 and FIG. 10A, this acceleration portion 100 is provided, for example, in one part of the jaw 52 located between a proximal end portion of the second electrode portion 53 and the rotation axis R in the axial direction of the movable handle unit 5. The acceleration portion 100 is formed by the deformation of one part of the jaw 52, is included in the jaw 52, and is integral with the jaw 52.

[Elastic Deformation Accelerated by the Acceleration Portion 100]

Elastic deformation in the grasping operation, elastic deformation when the grasping operation has finished, elastic deformation in the peeling operation, and elastic deformation when the peeling operation has finished are described below.

[Elastic Deformation During the Grasping Operation]

As shown in FIG. 10B, in the grasping operation, if the jaw 52 is closed to the probe 3 (moves in the arrow A1 direction), the second electrode portion 53 receives the reaction force F from the treatment target 150 in a direction opposite to the close direction, that is, in the open direction (the arrow A2 direction). Thus, in the grasping operation, the acceleration portion 100 accelerates the elastic deformation of the jaw 52 so that the jaw 52 is elastically deformed around the acceleration portion 100 in the open direction. In other words, in the grasping operation, the acceleration portion 100 accelerates the elastic deformation of the jaw 52 so that the second electrode portion 53 warps (flexes) around the acceleration portion 100 in the jaw 52 in the open direction, the second electrode portion 53 moves away from the first electrode portion 21, the jaw 52 changes from the straight state to the bent state, and the jaw 52 diverts the reaction force F.

[Elastic Deformation when the Grasping Operation has Finished]

As shown in FIG. 1 and FIG. 10A, when the grasping operation has finished and the reaction force F is no longer applied to the second electrode portion 53, the acceleration portion 100 accelerates the elastic deformation of the jaw 52 so that the jaw 52 is restored to the original state, that is, the second electrode portion 53 warps (flexes) around the acceleration portion 100 in the jaw 52 in the close direction (the arrow A1 direction), the second electrode portion 53 moves closer to the first electrode portion 21, and the jaw 52 changes from the bent state to the straight state.

[Elastic Deformation During the Peeling Operation]

As shown in FIG. 10C, in the peeling operation, if the jaw 52 is opened to the probe 3 (moves in the arrow A2 direction), the second electrode portion 53 receives the reaction force F from the treatment target 150 in a direction opposite to the open direction, that is, in the close direction (the arrow A1 direction). Thus, in the peeling operation, the acceleration portion 100 accelerates the elastic deformation of the jaw 52 so that the jaw 52 is elastically deformed around the acceleration portion 100 in the close direction. In other words, in the peeling operation, the acceleration portion 100 accelerates the elastic deformation of the jaw 52 so that the second electrode portion 53 warps (flexes) around the acceleration portion 100 in the jaw 52 in the close direction, the second electrode portion 53 moves closer to the first electrode portion 21, the jaw 52 changes from the straight state to the bent state, and the jaw 52 diverts the reaction force F.

[Elastic Deformation when the Peeling Operation has Finished]

As shown in FIG. 1 and FIG. 10A, when the peeling operation has finished and the reaction force F is no longer applied to the second electrode portion 53, the acceleration portion 100 accelerates the elastic deformation of the jaw 52 so that the jaw 52 is restored to the original state, that is, the second electrode portion 53 warps (flexes) around the acceleration portion 100 in the jaw 52 in the open direction (the arrow A2 direction), the second electrode portion 53 moves away from the first electrode portion 21, and the jaw 52 changes from the bent state to the straight state.

[Summary 1—Elastic Deformation During the Treatment Operation]

Thus, as shown FIG. 10B and FIG. 10C, if the jaw 52 opens and closes to the probe 3 (moves in the arrow A1 direction or the arrow A2 direction) during the treatment operation, the second electrode portion 53 receives the reaction force F from the treatment target 150 in a direction opposite to the open-close direction, that is, in the close-open direction (the arrow A2 direction or the arrow A1 direction). Thus, the acceleration portion 100 accelerates the elastic deformation of the jaw 52 so that the jaw 52 is elastically deformed in the direction in which the jaw 52 has received the reaction force F. In other words, the acceleration portion 100 accelerates the elastic deformation of the jaw 52 so that the second electrode portion 53 warps (flexes) around the acceleration portion 100 in the jaw 52 in the direction in which the jaw 52 has received the reaction force F and the jaw 52 diverts the reaction force F.

[Summary 2—Elastic Deformation when the Treatment Operation has Finished]

As shown in FIG. 1 and FIG. 10A, when the treatment operation has finished, the acceleration portion 100 accelerates the elastic deformation of the jaw 52 so that the jaw 52 is elastically deformed in a direction opposite to the direction in which the jaw 52 has received the reaction force F. In other words, the acceleration portion 100 accelerates the elastic deformation of the jaw 52 so that the second electrode portion 53 warps (flexes) around the acceleration portion 100 in the jaw 52 in the direction opposite to the direction in which the jaw 52 has received the reaction force F and the jaw 52 changes from the bent state to the straight state.

[Configuration of the Acceleration Portion 100]

As shown in FIG. 10A, the acceleration portion 100 has a thickness-reduced portion 101 which is easily elastically deformed so that the jaw 52 is easily elastically deformed. The thickness-reduced portion 101 is formed by reducing the thickness of the jaw 52 in the acceleration portion 100 in comparison with the thickness of the jaw 52 in parts other than the acceleration portion 100 so that the jaw 52 is elastically deformed around the acceleration portion 100. The thickness of the jaw 52 in the thickness-reduced portion 101 has only to be reduced in comparison with the thickness of the jaw 52 around the thickness-reduced portion 101 other than the thickness-reduced portion 101. The part around the thickness-reduced portion 101 represents, for example, the jaw 52 between the rotation axis R and the acceleration portion 100, and the jaw 52 between the second electrode portion 53 side which functions as the action point and the acceleration portion 100. The thickness-reduced portion 101 is directly provided, for example, in one part of the jaw 52. The thickness-reduced portion 101 is provided to function as a detour portion in which one part of the jaw 52 is corrugated along a central axis direction of the jaw 52. For example, one part of the jaw 52 in the detour portion is thinner than the other parts of the jaw 52. For example, the maximum thickness of one part of the jaw 52 in the detour portion is substantially the same as the maximum thickness of the other parts of the jaw 52.

Thus, as shown in FIG. 10A, the thickness-reduced portion 101 has open-side slots 103a which are depressed from an open-direction-side end face of the jaw 52 toward a close-direction-side end face of the jaw 52, and close-side slots 103b which are depressed from the close-direction-side end face toward the open-direction-side end face. The open-direction-side end face is, for example, a front surface of the jaw 52, and the close-direction-side end face is, for example, a rear surface of the jaw 52. The open-direction-side end face does not contact the treatment target 150 during the grasping operation, and contacts the treatment target 150 during the peeling operation. The close-direction-side end face contacts the treatment target 150 during the grasping operation, and does not contact the treatment target 150 during the peeling operation. The open-side slots 103a and the close-side slots 103b are alternately provided in the central axis direction of the jaw 52. The number of the open-side slots 103a is preferably the same as the number of the close-side slots 103b. The depth of the open-side slot 103a is preferably the same as the depth of the close-side slot 103b. The length of the open-side slot 103a is preferably the same as the length of the close-side slot 103b. The open-side slots 103a and the close-side slots 103b are provided to intersect at right angle with the central axis direction of the jaw 52, and are provided along a thickness direction of the jaw 2. The open-side slots 103a and the close-side slots 103b pass through the jaw 52 in a width direction of the jaw 52. The open-side slots 103a and the close-side slots 103b function as slits.

As shown in FIG. 10A, the thickness-reduced portion 101 has open-side thin portions 105a which are formed by providing the close-side slots 103b and which are provided on the open-direction-side end face side of the jaw 52, and close-side thin portions 105b which are formed by providing the open-side slots 103a and which are provided on the close-direction-side end face side of the jaw 52. The open-side thin portions 105a and the close-side thin portions 105b are alternately provided in the central axis direction of the jaw 52. The open-side thin portions 105a are provided, for example, higher than the central axis of the jaw 52 in the thickness direction of the jaw 52. The close-side thin portions 105b are provided, for example, lower than the central axis of the jaw 52 in the thickness direction of the jaw 52. The open-side thin portions 105a and the close-side thin portions 105b are formed by reducing the thickness of one part of the jaw 52 in comparison with the maximum thickness of the jaw 52, so that the jaw 52 is locally reduced in thickness. The width in the open-side thin portions 105a and the close-side thin portions 105b is equal to the width in the other parts of the jaw 52.

The close-side slot 103b is provided in alignment with the open-side thin portion 105a to face the open-side thin portion 105a in the thickness direction of the jaw 52 that intersects at right angles with the central axis of the jaw 52.

The open-side slot 103a is provided in alignment with the close-side thin portion 105b to face the close-side thin portion 105b in the thickness direction of the jaw 52.

As shown in FIG. 10A, the thickness-reduced portion 101 further has thick portions 107a which are contiguous to the open-side thin portions 105a and the close-side thin portions 105b and which have the same thickness as the other parts of the jaw 52. The thick portions 107a are provided along the thickness direction of the jaw 52.

In the central axis direction of the jaw 52, for example, the open-side slot 103a and the close-side thin portion 105b, the thick portion 107a, the close-side slot 103b and the open-side thin portion 105a, the thick portion 107a, the open-side slot 103a and the close-side thin portions 105b, the thick portion 107a, . . . are arranged in this order. The respective units are not particularly limited in number.

This acceleration portion 100 also functions as a local sectional portion which is a local reduction of the section of the jaw 52. The acceleration portion 100 varies the rigidity of one part of the jaw 52 in comparison with the rigidity of the other parts by the open-side slots 103a and the close-side slots 103b so that the rigidity of one part of the jaw 52 is lower than the rigidity of the other parts.

[Function]

[Function of Acceleration Portion 100 During the Grasping Operation]

As shown in FIG. 1, FIG. 10A, and FIG. 10B, if the movable handle 25 is closed to the fixed handle 22 and the jaw 52 is closed to the fixed handle 22 (moves in the arrow A1 direction), the second electrode portion 53 and the first electrode portion 21 grasp and sandwich the treatment target 150 therebetween together. At the same time, the second electrode portion 53 receives the reaction force F from the treatment target 150 in the open direction (the arrow A2 direction). In the grasping operation, the jaw 52 is then elastically deformed around the acceleration portion 100 in the open direction. At the same time, the elastic deformation is accelerated by the acceleration portion 100. In other words, in the grasping operation, the acceleration portion 100 accelerates the elastic deformation of the jaw 52 so that the second electrode portion 53 warps (flexes) around the acceleration portion 100 in the jaw 52 in the open direction, the second electrode portion 53 moves away from the first electrode portion 21, and the jaw 52 changes from the straight state to the bent state.

Therefore, even if the treatment target 150 is rigid and the reaction force F is great due to this rigidity, the elastic deformation accelerated by the acceleration portion 100 ensures that the jaw 52 can divert the reaction force F. Therefore, the jaw 52 is prevented gradual deformation of the jaw 52 by the reaction force F which the jaw 52 receives from the treatment target 150.

The second electrode portion 53 can also abut on the treatment target 150 along a circumferential surface of the treatment target 150 because the jaw 52 is elastically deformed. Thus, a grasping force can also be improved.

In the grasping operation shown FIG. 10B, the close-side slots 103b expand, and the open-side slots 103a narrow so that edges of the open-side slots 103a abut on each other, in the central axis direction of the jaw 52 (the length of the close-side slots 103b). The abutment of the edges of the open-side slots 103a prevents the jaw 52 from being extremely elastically deformed in the open direction, i.e., from bending around the acceleration portion 100.

[Function of Acceleration Portion 100 when the Grasping Operation has Finished]

As shown in FIG. 1 and FIG. 10A, if the grasping operation has finished, the movable handle 25 is opened to the fixed handle 22, the jaw 52 is opened to the probe 3, the second electrode portion 53 moves away from the treatment target 150, and the reaction force F is no longer applied to the second electrode portion 53. The jaw 52 is then elastically deformed around the acceleration portion 100 in the close direction. At the same time, the elastic deformation is accelerated by the acceleration portion 100. In other words, the acceleration portion 100 accelerates the elastic deformation of the jaw 52 so that the jaw 52 is restored to the original state, the second electrode portion 53 warps (flexes) around the acceleration portion 100 in the jaw 52 in the close direction, the second electrode portion 53 moves closer to the first electrode portion 21, and the jaw 52 changes from the bent state to the straight state.

This ensures that the jaw 52 which is elastically deformed around the acceleration portion 100 in the open direction in the grasping operation is elastically deformed in the close direction and is then restored to the original state in response to the finishing of the grasping operation. That is, if the grasping operation has finished, the jaw 52 does not keep the deformed state during the grasping operation. When the grasping operation is started again, the jaw 52 comes into the straight state which is the above-mentioned initial state, and the first electrode and the second electrode portion 53 grasp the treatment target 150 together in this initial state.

Consequently, even if the grasping operation is repeated, the deformation of the jaw 52 is prevented by the acceleration portion 100, and gradual deterioration of an operational force such as the grasping force is prevented.

For example, if the jaw 52 or the like is not restored to the original state from the deformed state during the grasping operation after the finishing of the grasping operation, the close amount in which the operator closes the movable handle 25 to the fixed handle 22 varies. Specifically, if the jaw 52 or the like is not restored to the original state from the deformed state during the grasping operation, there is concern that grasping force E1 before deformation may not be obtained even if the operator closes the movable handle 25 to the fixed handle 22 in a close amount A1 before deformation during the grasping operation. Thus, if the jaw 52 is not restored to the original state from the deformed state during the grasping operation, there is concern that the grasping force E1 may not be obtained unless the operator closes the movable handle 25 to the fixed handle 22 in a close amount A2 equal to or more than the close amount A1.

Therefore, there is concern that the operator may feel uncomfortable with the operation. If the grasping force corresponding to the close amount gradually deteriorates, there is concern that grasping operability may gradually deteriorate because of the lack of the recovery from the deformed state during the grasping operation to the original state.

However, in the present embodiment, gradual deterioration of the operational force such as the grasping force is prevented as described above. This prevents gradual deterioration of grasping operability resulting from the deterioration of the operational force such as the grasping force.

[Function of Acceleration Portion 100 During the Peeling Operation]

As shown in FIG. 1, FIG. 10A, and FIG. 10C, if the movable handle 25 is opened to the fixed handle 22 and the jaw 52 is opened to the probe 3 (moves in the arrow A2 direction), the second electrode portion 53 and the first electrode portion 21 peel the treatment target 150 together. At the same time, the second electrode portion 53 receives the reaction force F from the treatment target. 150 in the close direction (the arrow A1 direction). Thus, in the peeling operation, the jaw 52 is elastically deformed around the acceleration portion 100 in the close direction. At the same time, the elastic deformation is accelerated by the acceleration portion 100. In other words, in the peeling operation, the acceleration portion 100 accelerates the elastic deformation of the jaw 52 so that the second electrode portion 53 warps (flexes) around the acceleration portion 100 in the jaw 52 in the close direction, the second electrode portion 53 moves closer to the first electrode portion 21, and the jaw 52 changes from the straight state to the bent state.

Therefore, even if the treatment target 150 is rigid and the reaction force F is great due to this rigidity, the elastic deformation accelerated by the acceleration portion 100 ensures that the jaw 52 can divert the reaction force F. Therefore, the jaw 52 is prevented gradual deformation of the jaw 52 by the reaction force F which the jaw 52 receives from the treatment target 150.

The second electrode portion 53 can also abut on the treatment target 150 along the circumferential surface of the treatment target 150 because the jaw 52 is elastically deformed. Thus, a peeling force can also be improved.

In the peeling operation shown FIG. 10C, the open-side slots 103a expand, and the close-side slots 103b narrow so that edges of the close-side slots 103b abut on each other, in the central axis direction of the jaw 52 (the length of the close-side slots 103b). The abutment of the edges of the close-side slots 103b prevents the jaw 52 from being extremely elastically deformed in the close direction, i.e., from bending around the acceleration portion 100.

[Function of Acceleration Portion 100 when the Peeling Operation has Finished]

As shown in FIG. 1 and FIG. 10A, if the peeling operation has finished, the movable handle 25 is closed to the fixed handle 22, the jaw 52 is closed to the probe 3, the second electrode portion 53 moves away from the treatment target 150, and the reaction force F is no longer applied to the second electrode portion 53. The jaw 52 is then elastically deformed around the acceleration portion 100 in the open direction. At the same time, the elastic deformation is accelerated by the acceleration portion 100. In other words, the acceleration portion 100 accelerates the elastic deformation of the jaw 52 so that the jaw 52 is restored to the original state, the second electrode portion 53 warps (flexes) around the acceleration portion 100 in the jaw 52 in the open direction, the second electrode portion 53 moves away from the first electrode portion 21, and the jaw 52 changes from the bent state to the straight state.

This ensures that the jaw 52 which is elastically deformed around the acceleration portion 100 in the close direction in the peeling operation is elastically deformed in the open direction and is then restored to the original state in response to the finishing of the peeling operation. That is, if the peeling operation has finished, the jaw 52 does not keep the deformed state during the peeling operation. When the peeling operation is started again, the jaw 52 comes into the straight state which is the above-mentioned initial state, and the first electrode portion 21 and the second electrode portion 53 peel the treatment target 150 together in this initial state.

Consequently, even if the peeling operation is repeated, the deformation of the jaw 52 is prevented by the acceleration portion 100, and gradual deterioration of the operational force such as the peeling force is prevented.

For example, if the jaw 52 or like is not restored to the original state from the deformed state during the peeling operation after the finishing of the peeling operation, the open amount in which the operator opens the movable handle 25 to the fixed handle 22 varies. Specifically, if the jaw 52 or the like is not restored to the original state from the deformed state during the peeling operation, there is concern that peeling force B1 before deformation may not be obtained even if the operator opens the movable handle 25 to the fixed handle 22 in an open amount A1 before deformation during the peeling operation. Thus, if the jaw 52 is not restored to the original state from the deformed state during the peeling operation, there is concern that the peeling force B1 may not be obtained unless the operator opens the movable handle 25 to the fixed handle 22 in an open amount A2 equal to or more than the open amount A1.

Therefore, there is concern that the operator may feel uncomfortable with the operation. If the peeling force corresponding to the open amount gradually deteriorates, there is concern that peeling operability may gradually deteriorate because of the absence of the recovery from the deformed state to the original state during the peeling operation.

However, in the present embodiment, gradual deterioration of the operational force such as the peeling force is prevented as described above. This prevents gradual deterioration of peeling operability resulting from the deterioration of the operational force such as the peeling force.

Advantageous Effects

Thus, in the present embodiment, the jaw 52 can be elastically deformed by the acceleration portion 100. Therefore, even if the second electrode portion 53 receives the reaction force F from the treatment target 150 during a treatment operation such as the grasping operation and the peeling operation, the jaw 52 can divert the reaction force F in the direction in which the jaw 52 has received the reaction force F. This prevents the jaw 52 from being gradually deformed by the reaction force F from the treatment target 150. It is ensured that if the treatment operation has finished, the jaw 52 can be restored to the straight state which is the original state. When the treatment operation is started again, the jaw 52 comes into the straight state which is the above-mentioned initial state, and the first electrode portion 21 and the second electrode portion 53 can grasp the treatment target 150 together in this initial state.

That is, in the present embodiment, even if the treatment operation is repeated, the deformation of the jam 52 can be prevented by the acceleration portion 100, and gradual deterioration of a treatment force such as the grasping force and the peeling force can be prevented. As a result, in the present embodiment, resulting gradual deterioration of treatment operability can be prevented.

In the present embodiment, the jaw 52 can be elastically deformed by the acceleration portion 100. Therefore, in a treatment operation such as the grasping operation and the peeling operation, the second electrode portion 53 can abut on the treatment target 150 along the circumferential surface of the treatment target 150. Thus, in the present embodiment, the treatment force such as the grasping force and the peeling force can also be improved.

In general, when the movable handle unit 5 opens and closes to the sheath unit 4 during the treatment operation, the reaction force F is applied the most to the part between the second electrode portion 53 side which functions as the action point and the rotation axis R side which functions as the supporting point in the axial direction of the movable handle unit 5. In particular, the reaction force F is applied more to the rotation axis R side than to the second electrode portion 53 side. Thus, most of the load is applied to the jaw 52 when the reaction force F is applied to the jaw 52 in this part.

Thus, in the present embodiment, the acceleration portion 100 is provided closer to the rotation axis R side to the second electrode portion 53 side. Thus, the elastic deformation of the jaw 52 in this part can be accelerated, the jaw 52 can effectively divert the reaction force F, and the load on the jaw 52 can be reduced.

In the present embodiment, the acceleration portion 100 has the thickness-reduced portion 101 (a part of the jaw 52 which functions as the detour portion). Thus, in the present embodiment, in either the grasping operation or the peeling operation, the deformation of the jaw 52 can be prevented by the thickness-reduced portion 101, and gradual deterioration of the treatment force such as the grasping force and the peeling force can be prevented. Therefore, in the present embodiment, resulting gradual deterioration of treatment operability can be prevented.

In the present embodiment, the acceleration portion 100 has the open-side slots 103a and the close-side slots 103b which are depressed in the open-close direction of the jaw 52. Thus, in the present embodiment, the acceleration portion 100 can accelerate the elastic deformation of the jaw 52 so that the jaw 52 is elastically deformed in the direction in which the jaw 52 has received the reaction force F during the treatment operation. If the treatment operation has finished, the acceleration portion 100 can accelerate the elastic deformation of the jaw 52 so that the jaw 52 is elastically deformed in a direction opposite to the direction in which the jaw 52 has received the reaction force F.

In the present embodiment, when the movable handle 25 opens and closes to the fixed handle 22 in the grasping operation and the peeling operation, the acceleration portion 100 accelerates the elastic deformation of the jaw 52 so that direct transmission of an open-close force to the treatment target 150 via the second electrode portion 53 can be prevented. Thus, in the present embodiment, the acceleration portion 100 can prevent the open-close force from being directly transmitted to the treatment target 150 and excessively damaging the treatment target 150.

[First Modification]

As a first modification, as shown in FIG. 11A, the acceleration portion 100 may only have the close-side slots 103b, the open-side thin portions 105a, and the thick portions 107a. Multiple close-side slots 103b, multiple open-side thin portions 105a, and multiple thick portions 107a are provided. For example, the close-side slots 103b are provided at equal distance from one another in the central axis direction of the jaw 52. In the central axis direction of the jaw 52, for example, the close-side slot 103b and the open-side thin portion 105a, the thick portion 107a, the close-side slot 103b and the open-side thin portion 105a, the thick portion 107a, the close-side slot 103b and the open-side thin portion 105a, . . . are arranged in this order. The respective units are not particularly limited in number. Thus, an elastic deformation force representing a warping force in the grasping operation is different from an elastic deformation force representing a warping force in the peeling operation, and greater than the elastic deformation force in the peeling operation. An elastic deformation force representing a warping force when the grasping operation has finished is different from an elastic deformation force representing a warping force when the peeling operation has finished, and greater than the elastic deformation force in the peeling operation. Thus, elastic deformation can be varied in the treatment operation, and a configuration specialized for the grasping operation can be provided.

[Second Modification]

As a second modification, as shown in FIG. 11B, the acceleration portion 100 may only have the open-side slots 103a, the close-side thin portions 105b, and the thick portions 107a. Multiple open-side slots 103a, multiple close-side thin portions 105b, and multiple thick portions 107a are provided. For example, the open-side slots 103a are provided at equal distance from one another in the central axis direction of the jaw 52. In the central axis direction of the jaw 52, for example, the open-side slot 103a and the close-side thin portion 105b, the thick portion 107a, the open-side slot 103a and the close-side thin portion 105b, the thick portion 107a, . . . are arranged in this order. The respective units are not particularly limited in number. Thus, an elastic deformation force representing a warping force in the grasping operation is different from an elastic deformation force representing a warping force in the peeling operation, and smaller than the elastic deformation force in the peeling operation. An elastic deformation force representing a warping force when the grasping operation has finished is different from an elastic deformation force representing a warping force when the peeling operation has finished, and smaller than the elastic deformation force in the peeling operation. Thus, elastic deformation can be varied in the treatment operation, and a configuration specialized for the peeling operation can be provided.

Thus, the acceleration portion 100 has only to have at least one of the close-side slot 103b and the open-side slot 103a.

Multiple acceleration portions 100 may be discontinuously provided in the central axis direction of the jaw 52.

Second Embodiment

[Configuration]

The differences between the first embodiment and the second embodiment are only described below with reference to FIG. 12A, FIG. 12B, FIG. 12C, FIG. 12D, FIG. 12E, and FIG. 12F.

As shown in FIG. 12A, the thickness-reduced portion 101 according to the present embodiment is provided so that one part of the jaw 52 is formed to be thinner and flatter than the other parts of the jaw 52 in the open-close direction of the jaw 52. A central axis of the thickness-reduced portion 101 is coaxial with the central axis of the whole jaw 52. The section of the thickness-reduced portion 101 that intersects at right angles with the central axis of the jaw 52 has a symmetrical shape with respect to the central axis of the thickness-reduced portion 101 in a thickness direction of the thickness-reduced portion 101 which is the open-close direction. Thus, as shown in FIG. 12A and FIG. 12F, the open-side slot 103a and the close-side slot 103b are provided coaxially in the thickness direction of the jaw 52. The section has, for example, one of a rectangular shape shown in FIG. 12B and FIG. 12F, a trapezoidal shape shown in FIG. 12C and FIG. 12D, and an elliptical shape shown in FIG. 12E. When the section has the trapezoidal shape as shown in FIG. 12C and FIG. 12D, an upper side may be shorter than a lower side as shown in FIG. 12C, or the upper side may be longer than the lower side as shown in FIG. 12D. The section has an upper surface which functions as the open-direction-side end face of the jaw 52, and a lower surface which functions as the close-direction-side end face of the jaw 52. The upper surface and the lower surface are flat surfaces.

When the section has, for example, the rectangular shape as shown in FIG. 12B and FIG. 12F, $H/W<1$ wherein W is the width of the section which is the length of the upper side and the lower side, and the height of the section is H.

The above-mentioned thickness-reduced portion 101 also functions as a small diameter portion in which one part of the jaw 52 is thinner than the other parts of the jaw 52.

Advantageous Effects

In the present embodiment, the configuration of the acceleration portion 100 can be simpler, and the acceleration portion 100 can be easily formed.

In the present embodiment, the central axis of the thickness-reduced portion 101 is parallel to the central axis of the whole jaw 52, and the section has a symmetrical shape. This ensures that, for example, same warping amount (flexing amount) in the grasping operation and the peeling operation can be obtained, the warping amount is the elastic deformation amount, and, for example, same return amount when the grasping operation has finished and when the peeling operation has finished can be obtained, the return amount is the elastic deformation amount.

Multiple acceleration portions 100 may be provided in the central axis direction of the jaw 52. In this case, it is preferable that the acceleration portions 100 are provided at equal distance from one another in the central axis direction of the jaw 52.

Third Embodiment

[Configuration]

The differences between the first embodiment and the third embodiment are only described below with reference to FIG. 13.

The thickness-reduced portion 101 according to the present embodiment is provided so that one part of the jaw 52 functions as the detour portion which is corrugated along a direction that intersects at right angles with the central axis direction of the jaw 52. In this case, the open-side slot 103a and the close-side slot 103b are, for example, L-shaped. The open-side thin portion 105a and the close-side thin portion 105b are, for example, L-shaped.

In the open-side slot 103a, one side of the L-shape is provided to intersect at right angles with the central axis direction of the jaw 52, and the other side of the L-shape is provided along the central axis direction of the jaw 52.

In the close-side slot 103b, one side of the L-shape is provided to intersect at right angles with the central axis direction of the jaw 52, and the other side of the L-shape is provided along the central axis direction of the jaw 52.

In the above, the other sides of the L-shapes are adjacently provided in a direction that intersects at right angles with the central axis direction of the jaw 52.

The thickness-reduced portion 101 further has a thickness portion 107b which is contiguous to the open-side thin portion 105a and the close-side thin portion 105b and which is provided along the central axis direction of the jaw 52.

Advantageous Effects

In the present embodiment, advantageous effects similar to those according to the first embodiment can be obtained.

Fourth Embodiment

[Configuration]

The differences between the first embodiment and the fourth embodiment are only described below with reference to FIG. 14.

The acceleration portion 100 may be provided in the second electrode portion 53 which functions as the distal end portion of the jaw 52. In this case, the acceleration portion 100 has a cutout portion 109 which is provided along the central axis direction of the jaw 52 and which is formed by cutting out one part of the distal end portion of the jaw 52. The cutout portion 109 is provided at the proximal end portion of the second electrode portion 53 which is a fundamental part of the distal end portion of the jaw 52.

Advantageous Effects

In the present embodiment, the acceleration portions 100 are provided at the distal end portion of the jaw 52 and in the jaw 52, so that two elastically deformable parts are provided. This ensures that the deformation of the jaw 52 can be prevented by the acceleration portion 100 and that gradual deterioration of the operational force such as the grasping force and the peeling force can be prevented even if the treatment operation is repeated in the present embodiment. Therefore, in the present embodiment, gradual deterioration of operability can be prevented. In a treatment operation such as the grasping operation and the peeling operation, the second electrode portion 53 can abut on the treatment target along the circumferential surface of the treatment target.

In the present embodiment, in the grasping operation, the cutout portion 109 accelerates the elastic deformation of the second electrode portion 53, and the thickness-reduced portion 101 accelerates the elastic deformation of the jaw 52. Thus, in the present embodiment, the load on the jaw 52 can be further reduced in the grasping operation.

Fifth Embodiment

[Configuration]

Figure 15A:
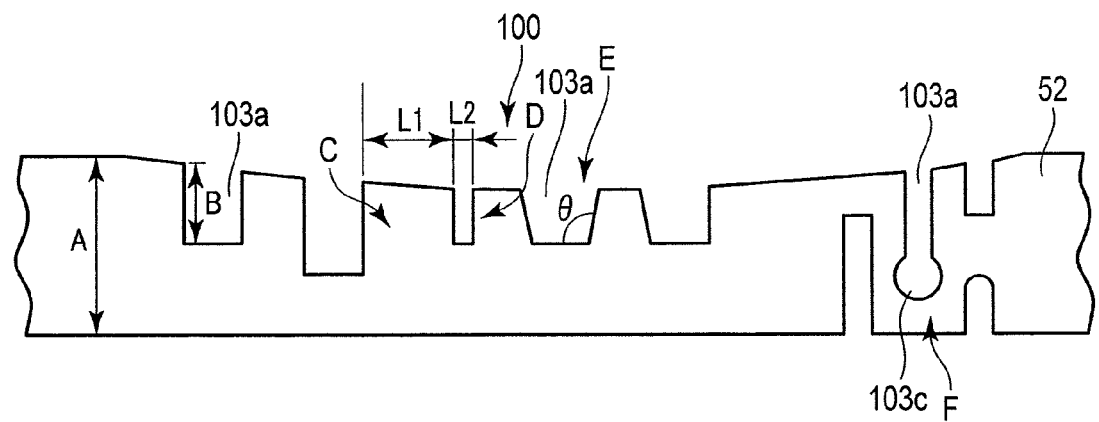
FIG. 15A is a diagram showing one example of a component of the acceleration portion according to a fifth embodiment.
Figure 15B:
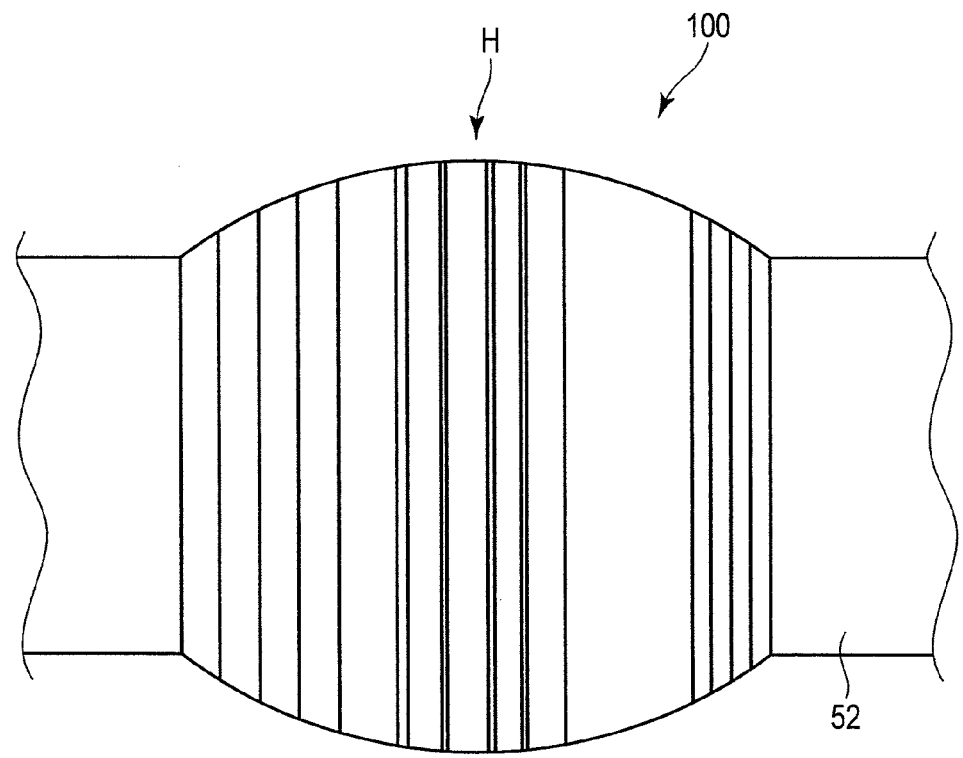
FIG. 15B is a diagram showing a configuration of the acceleration portion according to the fifth embodiment.

The differences between the first embodiment and the fifth embodiment are only described below with reference to FIG. 15A and FIG. 15B.

In the present embodiment, modifications of the acceleration portion 100 are described.

A: As shown in FIG. 15A, for example, the thickness the acceleration portion 100 may be varied in the central axis direction of the jaw 52 so that the thickness increases from the distal end portion of the acceleration portion 100 toward the proximal end portion of the acceleration portion 100. Thus, the elastic deformation amount can be adjusted.

B: As shown in FIG. 15A, the depth of one open-side slot 103a may be varied so that the distal end portion side of the open-side slot 103a is shallower and the proximal end portion side of the open-side slot 103a is deeper in the central axis direction of the jaw 52. Although not shown, the depths of the open-side slots 103a may be varied so that the open-side slots 103a provided on the distal end portion side of the acceleration portion 100 are shallower and the open-side slots 103a provided on the proximal end portion side of the acceleration portion 100 are deeper in the central axis direction of the jaw 52. Thus, the elastic deformation amount can be adjusted. The same also applies to the close-side slots 103b.

C: As shown in FIG. 15A, a distance L1 between one open-side slot 103a and the other open-side slot 103a may be varied in the central axis direction of the jaw 52. Thus, the elastic deformation amount can be adjusted. The same also applies to the close-side slots 103b.

D: As shown in FIG. 15A, a length L2 of each open-side slot 103a may be varied in the central axis direction of the jaw 52. Thus, the elastic deformation amount can be adjusted. The short length of the open-side slot 103a can prevent the treatment target from being caught in the open-side slot 103a. The same also applies to the close-side slots 103b.

E: As shown in FIG. 15A, an angle θ formed between the side surface of the open-side slot 103a and the bottom surface of the open-side slot 103a may be varied in the open-side slot 103a. Thus, the elastic deformation amount can be adjusted. Concentration of stress in the acceleration portion 100 can be reduced. It is possible to prevent the treatment target from being caught in the open-side slot 103a. The same also applies to the close-side slots 103b.

F: As shown in FIG. 15A, the open-side slot 103a may have a bending surface 103c provided on the bottom of the open-side slot 103a. Thus, the elastic deformation amount can be adjusted. The same also applies to the close-side slots 103b.

G: The number of the open-side slots 103a is not particularly limited. Thus, the elastic deformation amount can be adjusted. The same also applies to the close-side slots 103b.

H: As shown in FIG. 15B, the width of the acceleration portion 100 may be varied in comparison to the width of the other parts of the jaw 52 so that the width of the acceleration portion 100 is greater than the width of the other parts of the jaw 52. This makes it possible to gain flattening (H/L), and vary the elastic deformation force in the open-close direction.

The present invention is not completely limited to the embodiments described above, and modifications of components can be made at the stage of carrying out the invention without departing from the spirit thereof. Various inventions can be made by properly combining the components disclosed in the embodiments described above.

What is claimed is:

1. An energy treatment device comprising:
    a probe which extends along a longitudinal axis;
    a sheath unit into which the probe is inserted so that a distal end portion of the probe protrudes from a distal end of the sheath unit;
    a fixed handle which is provided in a proximal end portion of the sheath unit;
    a movable handle unit which is configured to open and close with respect to the fixed handle;
    a rotation axis which is provided in a position where the sheath unit and the movable handle unit intersect with each other and which functions as a supporting point for opening and closing the movable handle unit with respect to the fixed handle; and
    a jaw which is provided on a distal end portion of the movable handle unit and which is configured to open and close with respect to the distal end portion of the probe in accordance with the opening and closing of the movable handle unit;
    wherein the jaw comprises a thickness-reduced portion which is provided between the rotation axis and a distal end of the jaw, and wherein when one part of the jaw receives a reaction force from a treatment target when the movable handle unit closes with respect to the treatment target, the thickness-reduced portion is configured to flex in response to the reaction force when the one part of the jaw receives the reaction force from the treatment target, and the thickness-reduced portion is configured to prevent deformation of other parts of the jaw by flexing;
    wherein the jaw has a close-direction-side end face which faces the sheath unit, and an open-direction-side end face which is opposite to the close-direction-side end face;
    wherein the thickness-reduced portion comprises:
        at least one open-side slot which is depressed from the open-direction-side end face toward the close-direction-side end face; and
        at least one close-side slot which is depressed from the close-direction-side end face toward the open-direction-side end face; and
    wherein the open-side slot and the close-side slot are provided along a central axis direction of the jaw.

2. The energy treatment device according to claim 1, wherein when the reaction force disappears, the flexing is eliminated, and the thickness-reduced portion is restored to a state before occurrence of the flexing.

3. The energy treatment device according to claim 1, wherein the thickness-reduced portion functions as a detour portion which is corrugated along the central axis direction of the jaw.

4. The energy treatment device according to claim 1, wherein a sectional area of the thickness-reduced portion that intersects at right angles with the central axis direction of the jaw is smaller than a sectional area of the jaw that intersects at right angles with the central axis direction in parts other than the thickness-reduced portion.

5. The energy treatment device according to claim 4, wherein a sectional shape of the thickness-reduced portion is rectangular, trapezoidal, or elliptical.

6. The energy treatment device according to claim 1, wherein:
    the at least one open-side slot is depressed in an L-shape from the open-direction-side end face toward the close-direction-side end face, and
    the at least one close-side slot is depressed in an L-shape from the close-direction-side end face toward the open-direction-side end face.

7. The energy treatment device according to claim 1, further comprising a cutout portion formed in one part of a distal end portion of the jaw.

* * * * *